(12) United States Patent
Puleo et al.

(10) Patent No.: US 10,787,695 B2
(45) Date of Patent: Sep. 29, 2020

(54) SYSTEMS AND METHODS FOR RAPIDLY SENSING MICROBIAL METABOLISM

(71) Applicant: General Electric Company, Schenectady, NY (US)

(72) Inventors: Christopher Michael Puleo, Niskayuna, NY (US); Christine Lynne Surrette, Niskayuna, NY (US); Erik Leeming Kvam, Albany, NY (US); Steven Yuehin Go, Schenectady, NY (US); Feng Chen, Schenectady, NY (US); John Richard Nelson, Clifton Park, NY (US); Craig Patrick Galligan, Schenectady, NY (US); Radislav Alexandrovich Potyrailo, Niskayuna, NY (US); Gregory Andrew Grossmann, Halfmoon, NY (US)

(73) Assignee: General Electric Company, Schenectady, NY (US)

( * ) Notice: Subject to any disclaimer, the term of this patent is extended or adjusted under 35 U.S.C. 154(b) by 716 days.

(21) Appl. No.: 15/611,586

(22) Filed: Jun. 1, 2017

(65) Prior Publication Data
US 2018/0345278 A1    Dec. 6, 2018

(51) Int. Cl.
| | | |
|---|---|---|
| *C12Q 1/02* | (2006.01) | |
| *C12M 1/34* | (2006.01) | |
| *G01N 21/64* | (2006.01) | |
| *C12Q 1/18* | (2006.01) | |
| *G01N 33/483* | (2006.01) | |

(52) U.S. Cl.
CPC .............. *C12Q 1/02* (2013.01); *C12M 41/46* (2013.01); *C12M 41/00* (2013.01); *C12Q 1/18* (2013.01); *G01N 21/6408* (2013.01); *G01N 21/6452* (2013.01); *G01N 33/4836* (2013.01)

(58) Field of Classification Search
CPC ....................................................... C12Q 1/02
USPC ........................................................... 702/19
See application file for complete search history.

(56) References Cited

U.S. PATENT DOCUMENTS

| | | |
|---|---|---|
| 6,716,620 B2 | 4/2004 | Bashir et al. |
| 7,341,841 B2 | 3/2008 | Metzger et al. |
| 7,582,415 B2 | 9/2009 | Straus |
| 2003/0082516 A1 | 5/2003 | Straus |
| 2005/0059105 A1 | 3/2005 | Alocilja et al. |
| 2015/0064703 A1 | 3/2015 | Super et al. |
| 2015/0167043 A1 | 6/2015 | Goluch et al. |
| 2015/0247819 A1 | 9/2015 | Shi et al. |
| 2016/0067711 A1 | 3/2016 | Yoon et al. |
| 2016/0256870 A1* | 9/2016 | Ismagilov ......... B01L 3/502761 |

FOREIGN PATENT DOCUMENTS

| | | |
|---|---|---|
| CN | 1280404 C | 10/2006 |
| WO | 20160064838 A1 | 4/2016 |

OTHER PUBLICATIONS

Bashir, R., et al.; "Applications of Micro-systems Technology for Characterization and Detection of Microorganisms", Microelectromechanical Systems Conference, 2001, pp. 11-13, Aug. 24-26, 2001.

Boedicker, James Q., et al.; "Detecting Bacteria and Determining Their Susceptibility to Antibiotics by Stochastic Confinement in Nanoliter Droplets Using Plug-Based Microfluidics", Lab on a Chip, pp. 1265-1272, Issue 8, Aug. 2008.

Karnaushenko, Daniil, et al.; "Monitoring Microbial Metabolites Using an Inductively Coupled Resonance Circuit", Nature.com (Scientific Reports), vol. 5, Article No. 12878, Aug. 12, 2015.

* cited by examiner

Primary Examiner — Jerry Lin
(74) Attorney, Agent, or Firm — Eversheds Sutherland (US) LLP

(57) ABSTRACT

A system includes a bacteria culture array that includes a plurality of chambers each configured to receive a portion of a sample that includes bacteria. Each individual chamber of the plurality of chambers includes a chamber opening configured to permit access of the portion of the sample to the individual chamber. The system also includes one or more sensors configured to collect data from the individual chamber. The sensors are configured to contact the sample. Additionally, the system includes a monitoring and analysis system that includes a processor configured to receive the data from the one or more sensors at a first time and a second time, compare the data received at the second time to the data received at the first time, and identify a portion of the plurality of chambers of the bacteria culture array based on the comparing.

20 Claims, 24 Drawing Sheets

| T/S broth | Control strain (E. coli) | | | |
|---|---|---|---|---|
| -16106 | -91275 | -1800 | -44469 | -46559 |
| -11073 | -55464 | -49481 | -61992 | -54955 |
| -8463 | -78044 | -104556 | -48195 | -42547 |
| -9257 | -43356 | -19160 | -85373 | -6225 |
| -26130 | -101162 | -85373 | -80212 | -45262 |
| -3248 | -27162 | -37021 | -54243 | -46749 |
| -20896 | -51182 | -32008 | -66719 | |
| -11237 | -45500 | -42711 | -41639 | |

FIG. 36

| E. coli in amplicilin | | | | |
|---|---|---|---|---|
| -28401 | -29090 | -1251 | -119901 | -30346.4 |
| -77186 | -144281 | -686 | -123770 | -1001795 |
| -22496 | -75200 | 6381 | -30044 | 7598.103 |
| -37132 | -83374 | -24424 | -106180 | |
| -31385 | -117105 | -6844 | -10014 | |
| -30839 | -69136 | -10497 | 1023 | |
| -43702 | -82512 | -68771 | -318160 | |
| -144025 | -3909 | -18973 | 4373.282 | |

FIG. 37

| E. coli in kanamycin | | | | |
|---|---|---|---|---|
| | | | | |
| -59238.8 | -14877.3 | | | |
| -23005.5 | -6387.08 | | | |
| -28876 | -47242 | | | |
| -21158.9 | -39000.1 | | | |
| -28241.1 | -36078.7 | | | |
| -16898.6 | -7689.78 | | | |
| -14141.6 | | | | |
| 1177.785 | | | | |

# SYSTEMS AND METHODS FOR RAPIDLY SENSING MICROBIAL METABOLISM

STATEMENT REGARDING GOVERNMENT RIGHTS

This invention was made with support under Contract HDTRA1-16-C004 awarded by the Defense Threat Reduction Agency. The Government has certain rights in this invention.

BACKGROUND

The subject matter disclosed herein relates to pathogen diagnostics. More specifically, the subject matter disclosed herein relates to rapid bacteria monitoring and analysis.

Bacteria monitoring and analysis techniques may allow for determinations regarding bacteria to be made. For example, the determination may include identifying a type of bacteria and/or whether a bacterium is resistant to a certain antimicrobial agent. Present techniques for monitoring and analyzing bacteria typically have pre-culture steps so enough bacteria can be obtained to perform the techniques. Additionally, some techniques may call for obtaining certain information regarding the bacteria before the techniques may be executed. Moreover, in clinical settings, present techniques may take several days to obtain results.

BRIEF DESCRIPTION

In one embodiment, a system includes a bacteria culture array that includes a plurality of chambers each configured to receive a portion of a sample that includes bacteria. Each individual chamber of the plurality of chambers includes a chamber opening configured to permit access of the portion of the sample to the individual chamber. The system also includes one or more sensors configured to collect data from the individual chamber. The sensors are also configured to be in contact with the sample. Additionally, the system includes a monitoring and analysis system that includes a processor configured to receive the data from the one or more sensors at a first time and a second time, compare the data received at the second time to the data received at the first time, and identify a portion of the plurality of chambers of the bacteria culture array based on the comparing.

In another embodiment, a method includes providing a bacteria culture array that includes a plurality of individually addressable sensors. Each individual sensor of the plurality of individually addressable sensors is configured to be in contact with a respective sample site of the bacteria culture array. The method also includes contacting, at an initial time, the bacteria culture array with a sample that includes bacteria such that the sample is distributed throughout the bacteria culture array onto the respective sample sites and such that respective sample sites receive one bacterial cell or less from the sample. Additionally, the method includes receiving data from the plurality of individually addressable sensors over time. Moreover, the method includes comparing the data from the plurality of individually addressable sensors to a baseline representative of the initial time. The method also includes identifying individual sample sites in the bacteria culture array based on the comparing.

In yet another embodiment, a method includes loading a sample that includes bacteria into a plurality of chambers of a bacterial culture array via a filling channel such that a portion of the plurality of chambers comprises the sample. Each chamber of the plurality of chambers includes a sensor of a plurality of sensors configured to collect data regarding an electronic property of each respective chamber. Also, the method includes loading a fluid into the filling channel such that a meniscus is formed in each chamber of the portion of the plurality of chambers. The method also includes collecting data via the plurality of sensors.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 36 is a spreadsheet of resistance measurements from a bacteria culture array with chambers that included a growth medium and other chambers that included growth medium and bacteria, in accordance with embodiments described herein;

FIG. 37 is a spreadsheet 184 of resistance measurements taken from a bacteria culture array with chambers that included bacteria and an antimicrobial agent, in accordance with embodiments described herein;

DETAILED DESCRIPTION

Bacteria monitoring and analysis techniques may allow for determinations regarding bacteria to be made. The embodiments of the present application allow for the rapid, single cell, sensing of microbial metabolism. In other words, the embodiments of the present application allow for the culturing, monitoring, and analysis of individual bacterium in a matter of minutes or hours. More specifically, data may be collected, monitored, and analyzed in real time. Moreover, as discussed below, the embodiments of the present application may be used for monitoring and analyzing populations of bacteria. Furthermore, certain embodiments of the present application discussed are portable.

In certain embodiments, the present techniques facilitate determination of antimicrobial resistance and/or susceptibility profiles for bacteria present in patient-derived samples (e.g., saliva, urine, blood, etc.). Antimicrobials, which may also be referred to as antimicrobial agents, are agents (e.g., chemical agents) that kill microorganisms and/or limit the growth of microorganisms. In contrast to techniques in which bacteria present in such samples are cultured over a period of days before antimicrobial resistance is assessed, the present techniques permit assessment of the effect of antimicrobials on bacteria in shorter timeframes and at the point of care. Further, more rapid assessment of bacterial resistance may prevent over- and misuse of broad-spectrum antimicrobials. That is, rather than prescribing broad-spectrum antimicrobials in the intervening time period until culture results are complete, clinicians may more accurately prescribe the appropriate antimicrobial using antimicrobial resistance and/or susceptibility information as assessed using the present techniques.

Figure 1:
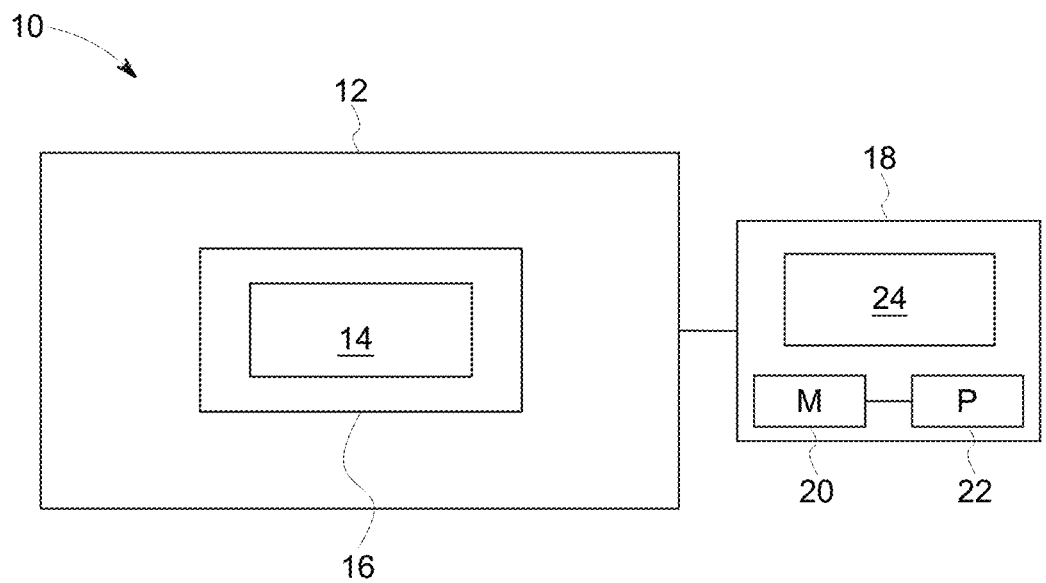
FIG. 1 is a schematic diagram of a bacteria monitoring and analysis system, in accordance with embodiments described herein.

By way of introduction, FIG. 1 is a schematic diagram of a bacteria monitoring and analysis system 10. The bacteria monitoring and analysis system 10 may include a device 12, which may include a sample 14 that may be monitored and analyzed by the monitoring and analysis system 10. As described below, the sample 14 may include bacteria and/or antimicrobial agents. Moreover, the sample 14 may be positioned within chambers of a bacteria culture array 16. As discussed below, the sample 14 within the bacteria culture array 16 may be monitored and analyzed in real time. For example, the individual bacterium may be disposed within the chambers of the bacteria culture array, and sensors may be used to collect data associated with the chambers (and the bacteria in the chambers).

Additionally, the bacteria monitoring and analysis system 10 may include a sample monitoring and analysis system 18 (e.g., an impedance analyzer or an inductance, capacitance, and resistance meter (also known as an LCR meter). The sample monitoring and analysis system 18 may collect data regarding the sample 14 and/or the bacteria culture array 16 and monitor and/or analyze the data in real time. For instance, the bacteria culture array 16 may include sensors that may send data to the sample monitoring and analysis system 18, which may perform calculations associated with the data. Furthermore, the sample monitoring and analysis system 18 may include memory 20 and a processor 22. The memory 20 may store data received from the sensors as well as instructions and steps written in software code. The processor 22 may execute the stored instructions in response to user input received via a user interface, such as a graphical user interface (GUI) 24. For example, the instructions stored on the memory 20, when executed by the processor 22, may allow for data collected from the sensors to be monitored and analyzed.

Figure 2:
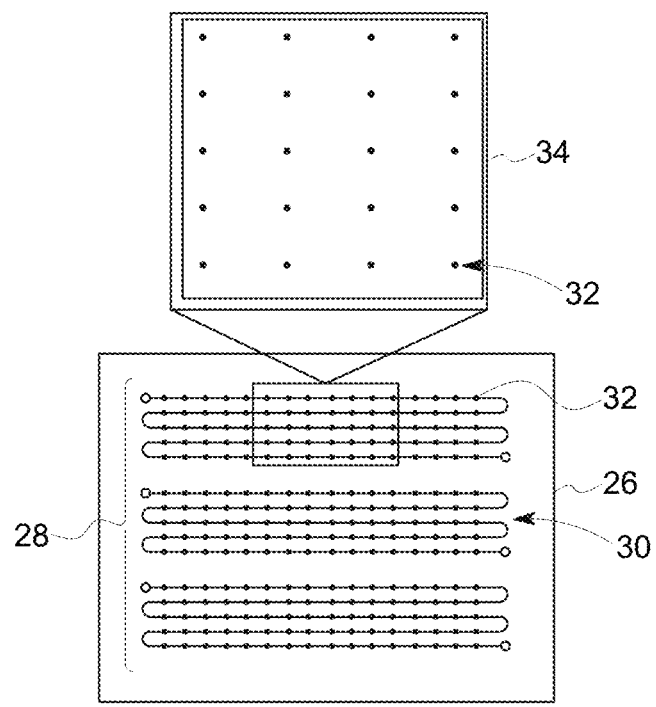
FIG. 2 is a diagram of a device with a bacteria culture array, in accordance with embodiments described herein.

FIG. 2 is a diagrammatical representation of a device 26 that includes a bacteria culture array 28. In some embodiments, the device 26 may be the device 12 of the bacteria monitoring and analysis system 10 or included in the device 12. The device 26, which may be portable and made of polydimethylsiloxane (PDMS), may include one or more filling channels 30 into which a sample may be added. More specifically, the filling channels 30 may make up an array of chambers 32, and bacteria from the sample may become disposed within the chambers 32. The illustrated arrangement of the chambers 32 is also illustrated within a zoomed in portion 34 of the array 32. The chambers 32 may be arranged uniformly on the device. For instance, as illustrated, the chambers 32 may be arranged in a grid-like manner. However, in other embodiments, the chambers 32 may be arranged in a non-uniform manner.

While the illustrated embodiment includes three filling channels 30, other embodiments of the device 26 may include less than or more than three filling channels 30. For instance, the device 26 may include one filling channel 30, while in another embodiment, the device may include five, ten, or more filling channels 30. Moreover, the bacteria culture array 28 may include any suitable number of chambers 32. Generally, the bacteria culture array may include one (1) to one-hundred thousand (100,000) chambers 32. For instance, in some embodiments, the bacteria culture array 28 may include a few (e.g., one, five, ten, or twenty) chambers, while other embodiments may include a much larger number of chambers 32 (e.g., three thousand, five thousand, ten thousand, or one-hundred thousand).

Figure 3:
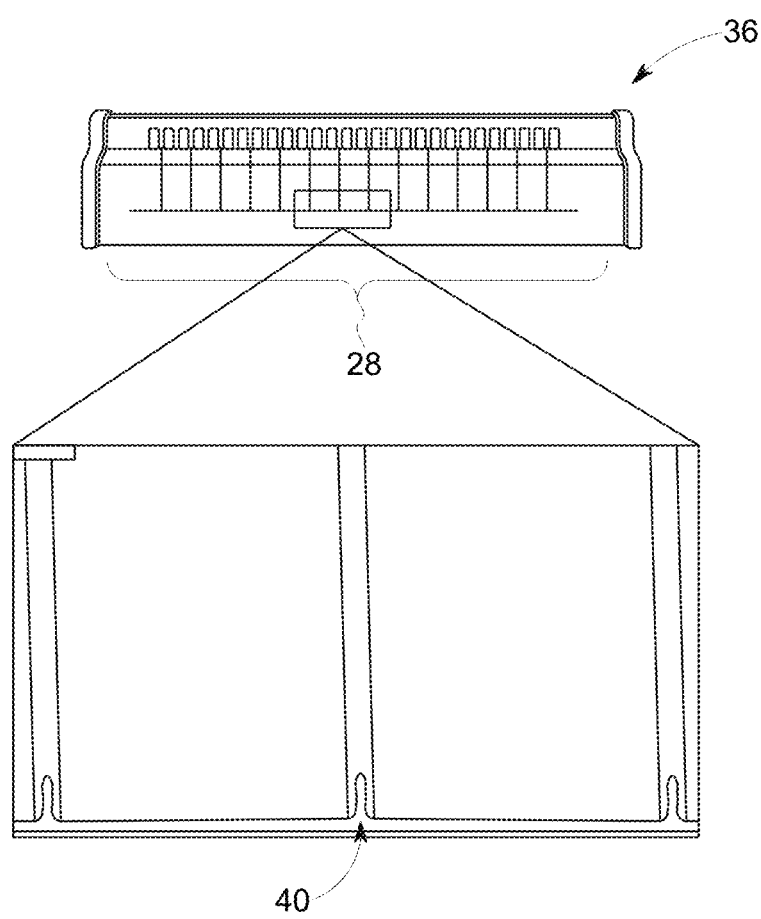
FIG. 3 is a perspective view of a microdevice that includes a bacteria culture array, in accordance with embodiments described herein.

FIG. 3 is a perspective view a microdevice 36 that includes a bacteria culture array 38. Similar to the device 26, the microdevice 36 may be used in the monitoring and analysis system 10. That is, bacteria may be added chambers 40 of the microdevice 36, and each of the chambers 40 may be monitored and analyzed in real time (e.g., by the sample monitoring and analysis system 18). It should be noted that loading of bacteria into the chambers 40 occurs in a Poisson distribution. Based on the concentration of bacteria in the sample (e.g., sample 14) the each of the chambers 40 may include bacteria within a certain range. Also similar to the device 26, the microdevice 36 may be made from PMDS. Furthermore, it should be noted that a sample may be loaded into chambers 40 of the microdevice 36 without first removing air from the within the microdevice 36 (e.g., air that occupies the chambers 40). The bacteria culture array 38 includes chambers 40. In one embodiment, the chambers 40 may range in volume from 1 picoliter to 50,000 picoliters, while in another embodiment the chambers may range in volume from 100 picoliters to 50,000 picoliters. Additionally, the chambers 40 may be aligned with, and bonded to, electrical sensors on a glass substrate. More specifically, each of the chambers 40 may be bonded to an electrical sensor using oxygen plasma bonding between the glass substrate and the PMDS of the microdevice 36. It should be noted that, in other embodiments, a plastic substrate may be used in place of a glass substrate.

Figure 4:
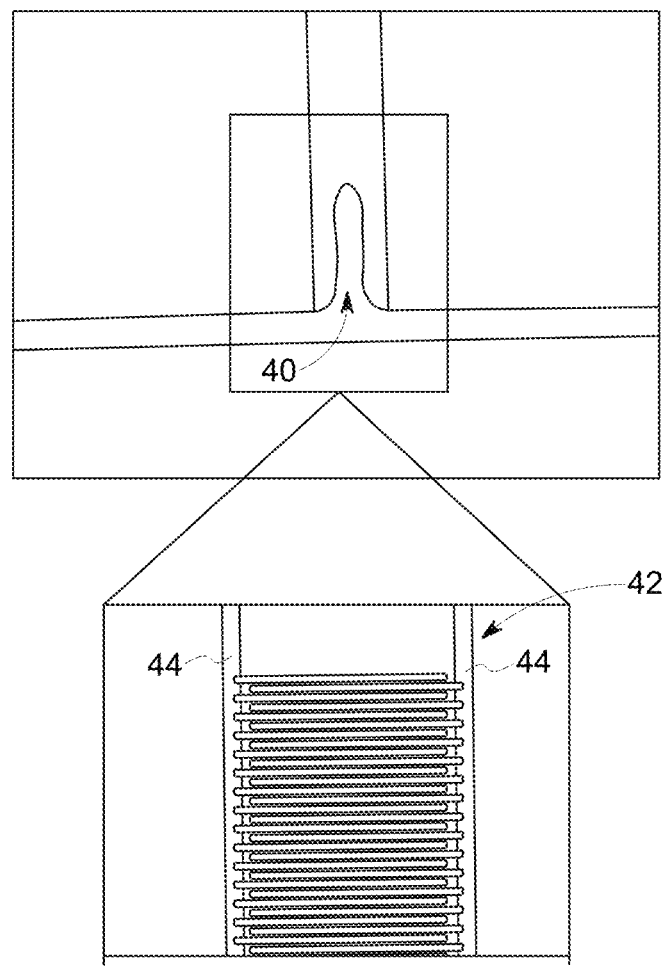
FIG. 4 is a diagram of an individual chamber of the bacteria culture array of FIG. 3 and a sensor that underlies the chamber, in accordance with embodiments described herein.

Keeping the microdevice 36 in mind, FIG. 4 is a diagram of the chamber 40 of the bacteria culture array 38 of FIG. 3 and a sensor 42 that underlies the chamber 40. More specifically, the sensor 42 includes two interdigitated electrodes 44 that are positioned underneath the chamber 40. The electrodes 44 may be made from various metals, such as platinum, gold, titanium, and passivated metals (e.g., stainless steel).

When the chamber 40 is filled (e.g., with a growth medium that includes bacteria), the electrodes 44 of the sensor 42 may contact the contents of the chamber 40. The electrodes 44 may be coupled to contact pads, which may be coupled to analytical equipment (e.g., the sample monitoring and analysis system 18). In this manner, data may be collected by the sensors 42 and transmitted to the analytical equipment, which may monitor and analyze the chamber 40. For instance, the sensor 42 may collect data regarding various electrical properties such as, but not limited to, impedance, capacitance, conductivity, and resistance, and the data may be monitored and analyzed by the analytical equipment.

Before continuing to the next drawing, it should be noted that the device 26 may operate in a similar manner as described above with regard to the microdevice 36. In other words, the device 26 may include sensors that underlie the chambers 32. The sensors may also be disposed within the chambers 32 and physically contact the sample that occupies the chambers 32. That is, the sensors may allow for the real time collection of data from each chamber 32 of the device 26.

Figure 5:
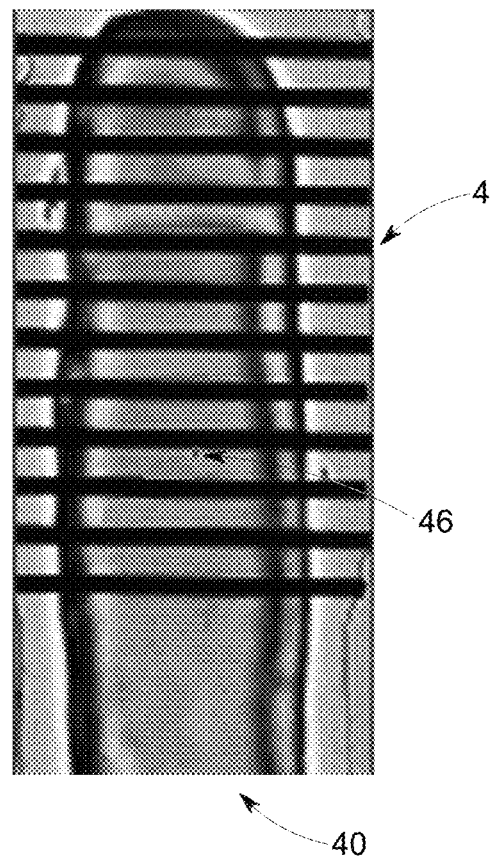
FIG. 5 is an image of an individual chamber of the bacteria culture array of FIG. 3 with an overlay representing the position of the sensor, in accordance with embodiments described herein.

FIG. 5 is an image of a chamber 40 of the bacteria culture array 38 with an overlay representing the position of a sensor 42. The chamber 40, as illustrated, is filled with a growth medium. Additionally, a bacterium 46 is disposed within the chamber 40. As explained above, the sensor 42 may collect data associated with the content of the chamber 40, including the bacterium 46. In other words, the microdevice 36, which includes the bacteria culture array 38, may be used to measure data regarding a single bacterium. Moreover, the sensors 42 may collect data associated with each of the chambers 40. Thus, if the chambers 40 each include bacteria 46, data regarding each of the bacteria 46 may be collected.

Figure 6:
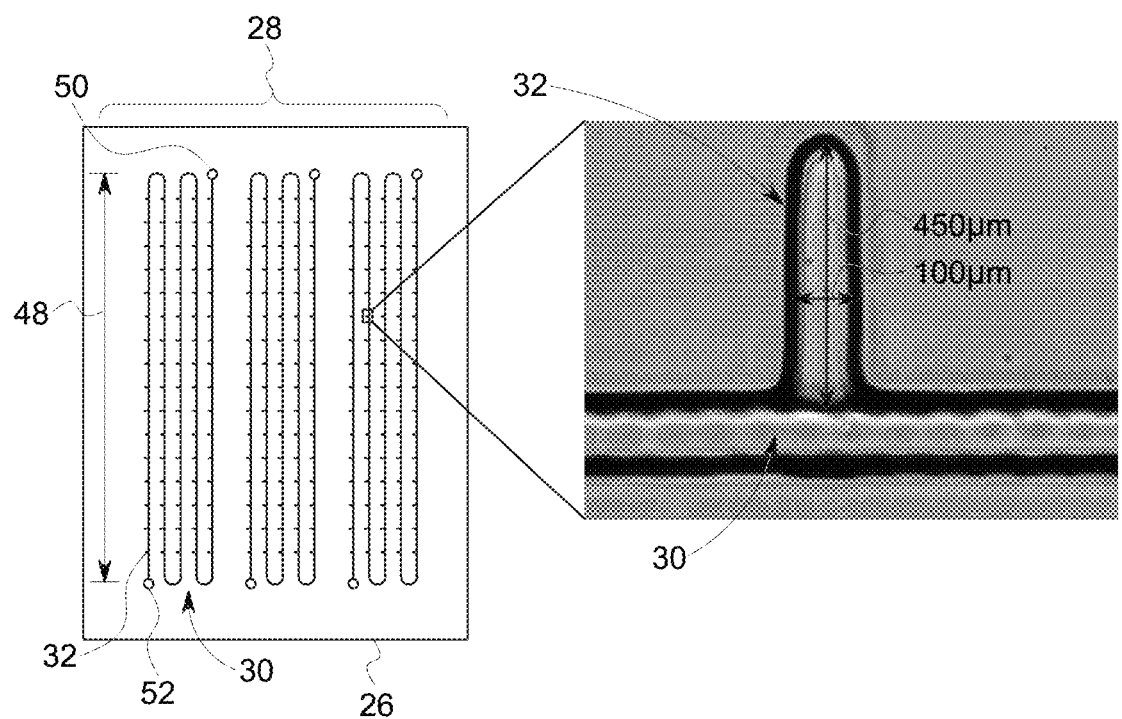
FIG. 6 is a diagram of the device of FIG. 2 with an image of a chamber of the device, in accordance with embodiments described herein.
Figure 7:
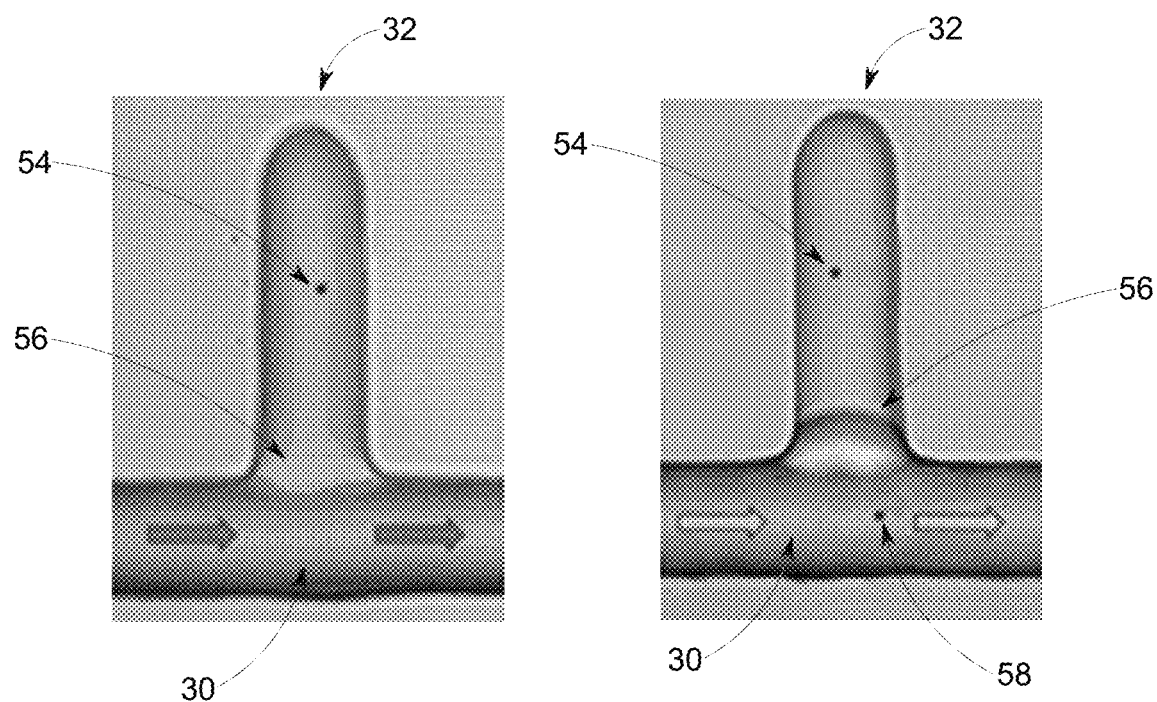
FIG. 7 is a diagram showing loading a chamber of a bacteria culture array, in accordance with embodiments described herein.

FIG. 6 and FIG. 7 relate to the loading of the device 26 with bacteria. More specifically, FIG. 6 is a diagram of the device 26 with an image of one of the chambers 32. Similar to the discussion of loading the microdevice 36 above, loading of the device 26 occurs in accordance with a Poisson distribution. That is, the amount of bacteria in chambers 32 after loading is based on the concentration of the bacteria in the sample. For instance, at certain concentrations, each of the chambers 32 may include no bacteria, a single bacteria cell, or more than one bacteria cell. The filling channels 30 of the bacteria culture array 28 of the device 26 may be filled with a sample (e.g., sample 14). For instance, air within a first column 48 of each filling channel 30 may be displaced with a sample to be monitored and/or analyzed by plugging an outlet 50 of the filling channel 30 and by applying pressure to an inlet 52 of the filling channel 30. The sample may continue to pass through the rest of the filling channel 30. Additionally, bacteria in the sample may enter the chambers 32 as the sample passes through the filling channel 30. When the bacteria culture array 28 is filled in such a manner, the amount of bacteria in each of the chambers 32 may be related to the starting concentration of bacteria in the sample that was added to the filling channel 30. The chambers 32 may each include one bacteria cell when a suitable starting concentration is used.

In the illustrated embodiment, the chamber 32 of the bacteria culture array 28 has a volume of approximately (±10%) four nanoliters (i.e., 4,000 picoliters). However, the chambers 32 may have volumes as small as 1 picoliter and volumes as large as 50,000 picoliters (i.e., 50 nanoliters) in other embodiments. In any case, data regarding the content of the chambers 32 may be collected in the manner described above. That is, a sensor may underlie a chamber 32, physically contact the contents of the chamber 32, and collect data regarding the content of the chamber 32.

FIG. 7 is a diagram of loading a chamber 32 of the bacteria culture array 28. More specifically, FIG. 7 illustrates that each chamber 32 of the bacteria culture array 28 may be isolated from the other chambers. As the sample runs through the filling channel 30, a bacterium 54 becomes disposed within a chamber 32. An oil phase may be added to the filling channel 30, which may cause an oil-water meniscus 56 to form, which may act as a barrier to isolate the contents of the chamber 32, including the bacterium 54, from the filling channel 30. It should also be noted that air, other gases, and liquids other than oil may be used in the alternative to oil. In other words, different fluids may be used in addition to oil to isolate each chamber 32. More of the sample may be added to the filling channel 30, and other bacteria (e.g., bacterium 58) may be prevented from entering the chamber 32 due to the meniscus 56. Additionally, the meniscus may define the ratio of the volume of the sample in a chamber 32 to the surface area of the sensor 42.

Figure 8:
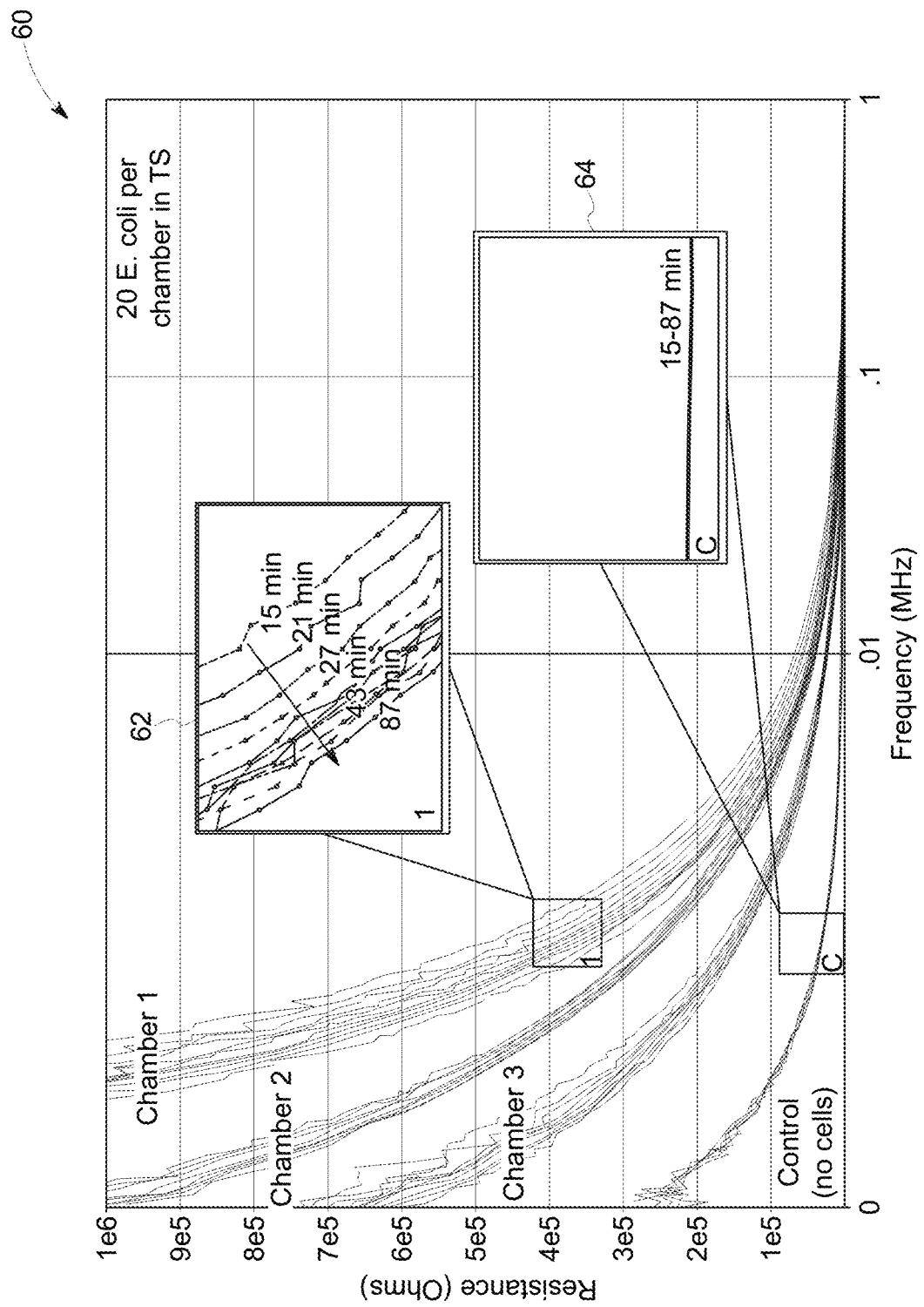
FIG. 8 is a graph showing changes in conductivity that occurs while bacteria grow within chambers of a bacteria culture array, in accordance with embodiments described herein.

As discussed above, data may be collected regarding the content of the chambers of the bacteria culture arrays. FIG. 8 is a graph 60 showing changes in conductivity that occurs while bacteria grow within chambers of a bacteria culture array. Chambers 1-3 were filled with approximately twenty *Escherichia coli* (*E. coli*) bacteria in tryptic soy broth. As shown in the zoomed-in portion 62 of the graph 60, there was a decrease in resistance (i.e., an increase in conductivity) over time in the chambers that included bacteria. However, as shown in the zoomed-in portion 64, there is no trend over time in the control (i.e., a chamber that did not include any bacteria).

As provided herein, a determination of resistance and/or susceptibility may be made by evaluating characteristic changes in measured sensor data that are associated with known results. For example, bacterial death as a result of contact with an antimicrobial agent may produce a characteristic curve or change in measured sensor output. As another example, bacterial growth and/or growth based on a type of growth medium may produce a characteristic curve or change in measured sensor output. A sample may be assessed by fitting an unknown sample to a characteristic curve. For instance, one may determine a type of bacteria present in the sample based on whether the data associated with the sample corresponds to a curve associated with bacterial growth or death.

Figure 9:
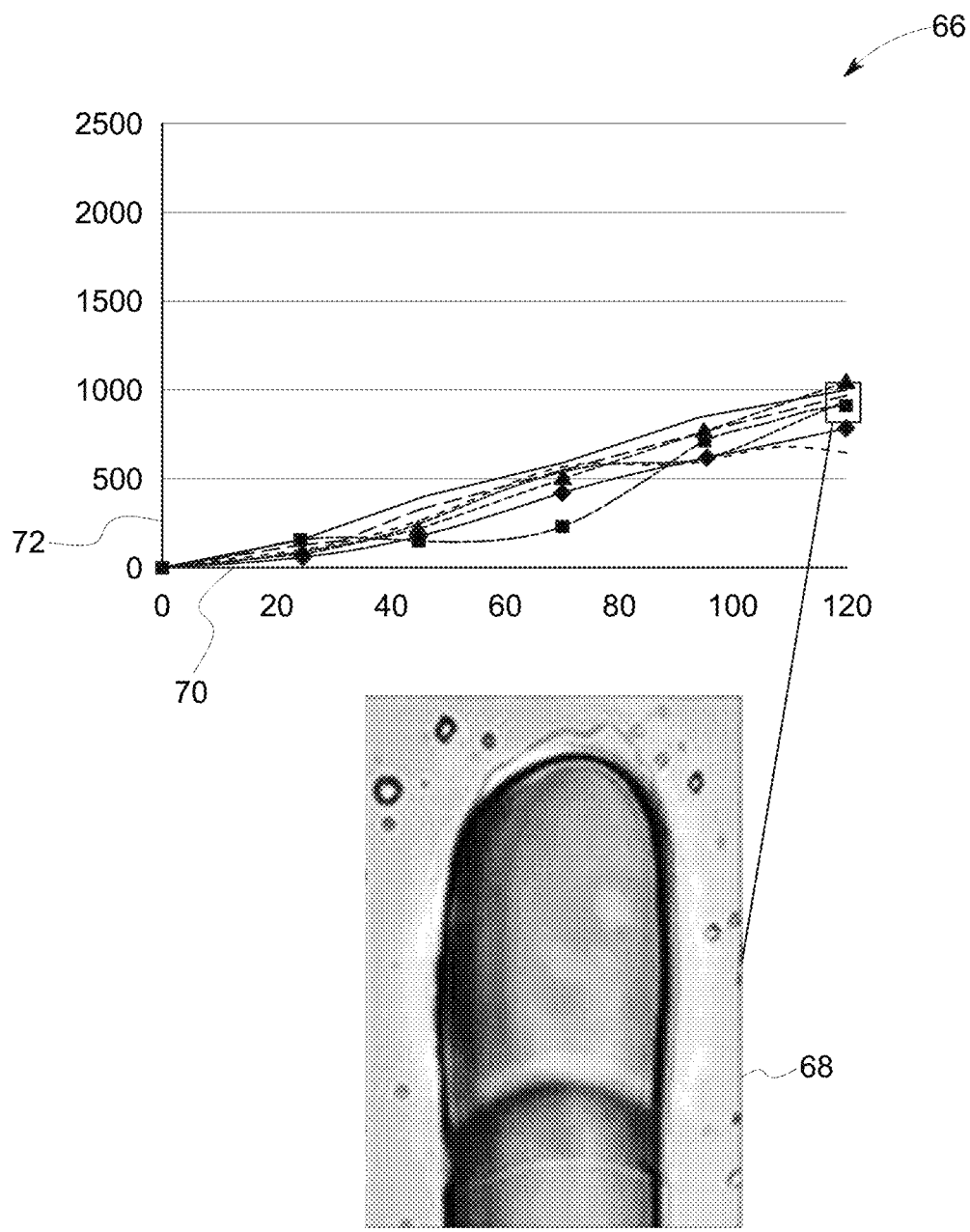
FIG. 9 is a graph showing fluorescence over time measured in chambers of a bacteria culture array that do not include bacteria, in accordance with embodiments described herein.

FIG. 9 is a graph of control data 66 showing fluorescence over time measured in chambers of a bacteria culture array that include a growth broth and a fluorescence indicator (e.g., resazurin) but not bacteria (as shown in image 68). A horizontal axis 70 is representative of time in minutes, while a vertical axis 72 is representative of intensity of fluorescence. The detected increase in fluorescence over time is likely due to evaporation of the aqueous solution within the well over time.

Figure 10:
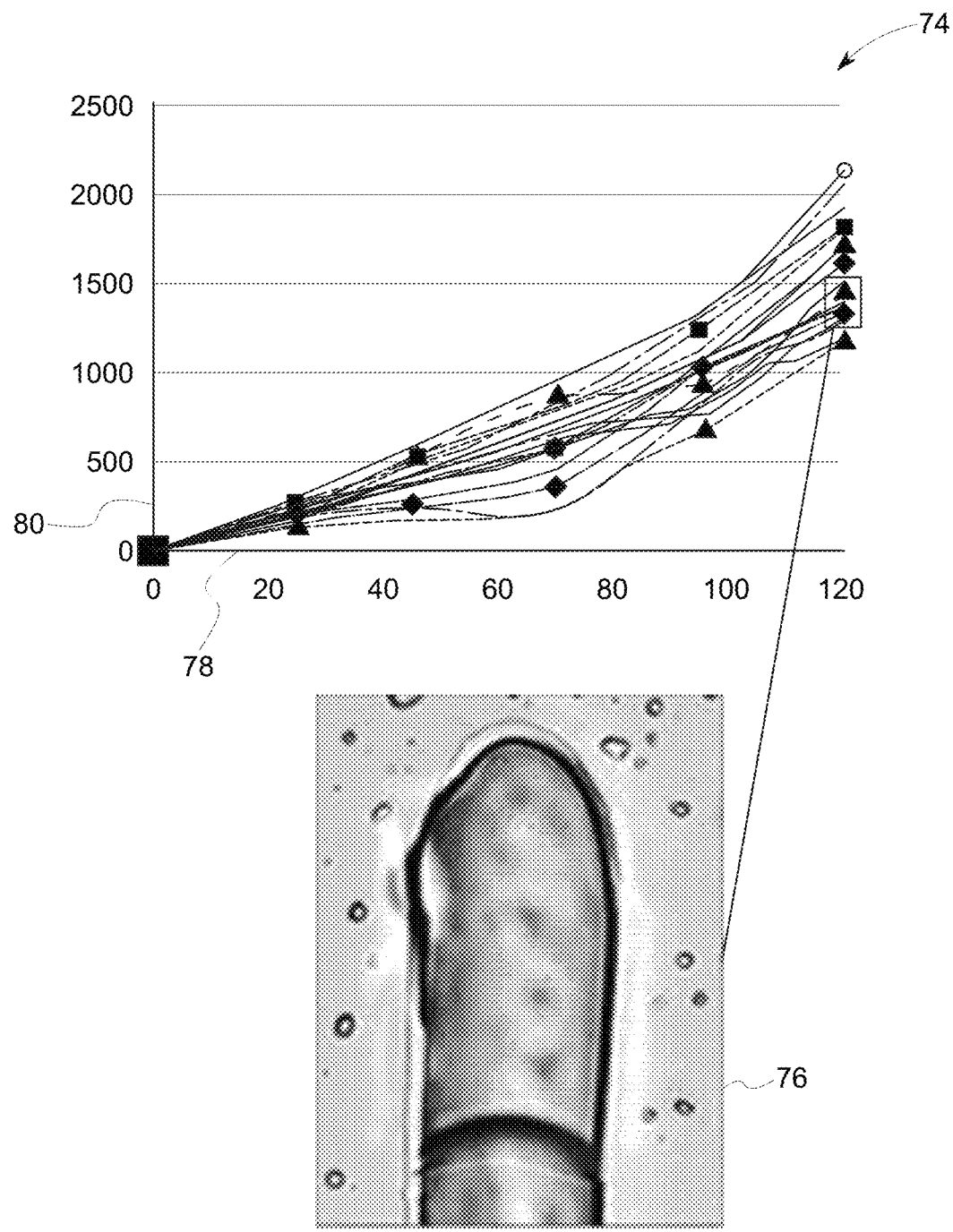
FIG. 10 is a graph showing fluorescence over time measure in chambers of a bacteria culture array that include bacteria, in accordance with embodiments described herein.

FIG. 10 is a graph of control data 74 showing fluorescence over time measure in chambers of a bacteria culture array that include bacteria (as shown in image 76) and the same growth broth and fluorescence indicator as the chambers indicated in the graph 66 of FIG. 9. A horizontal axis 78 is representative of time in minutes, while a vertical axis 80 is representative of intensity of fluorescence. As can be seen in comparison to graph 66, the fluorescence intensity measured within the chambers had a larger increase than in chambers without bacteria. This enables determination of bacteria-containing chambers and comparison to the electrical signals from the sensors.

Figure 11:
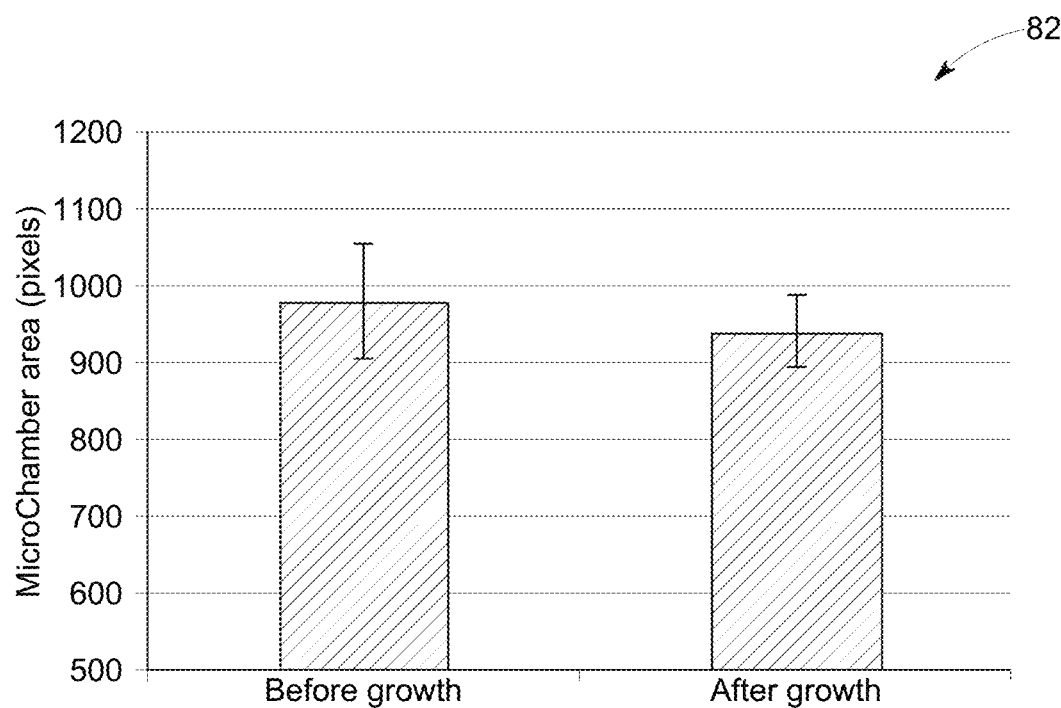
FIG. 11 is a bar graph showing average detected areas of chambers of a bacteria culture array before and after bacteria was cultured in the bacteria culture array, in accordance with embodiments described herein.

Keeping the evaporation discussed in relation to FIG. 8 in mind, FIG. 11 is a graph 82 showing an average detected area of chambers of a bacteria culture array before and after growth of bacteria in the chamber. The bacteria culture array that included the chambers was surrounded by a plastic jacket that was filled with saline solution to prevent evaporation. For instance, the bacteria culture array may have been included within the microdevice 36. The graph 82 indicates that the average size of the chambers was not statistically different when evaporation was prevented.

Figure 12:
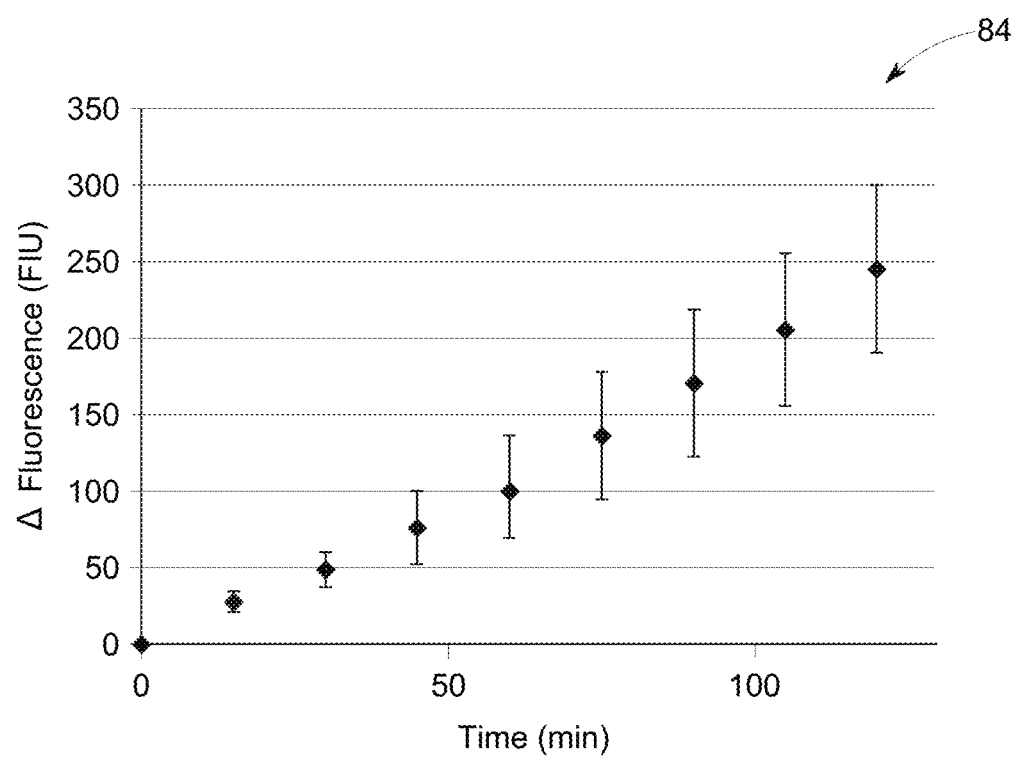
FIG. 12 is a graph showing fluorescence over time of chambers of a bacteria culture array that include bacteria, in accordance with embodiments described herein.
Figure 13:
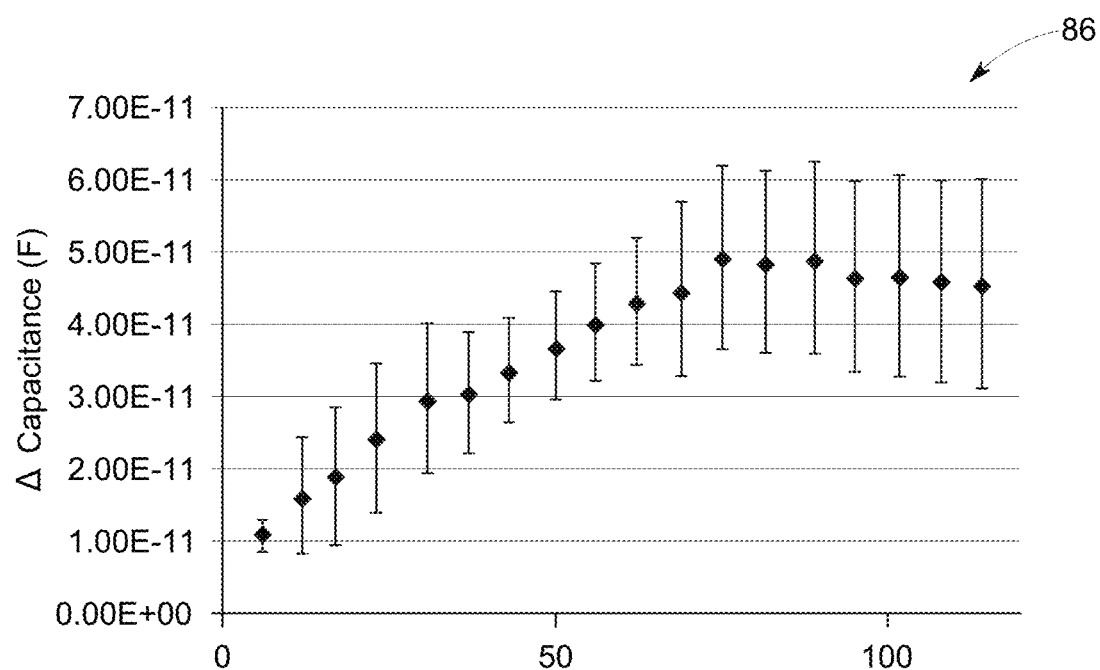
FIG. 13 is a graph showing capacitance over time of the chambers of the bacteria culture array of FIG. 12, in accordance with embodiments described herein.
Figure 14:
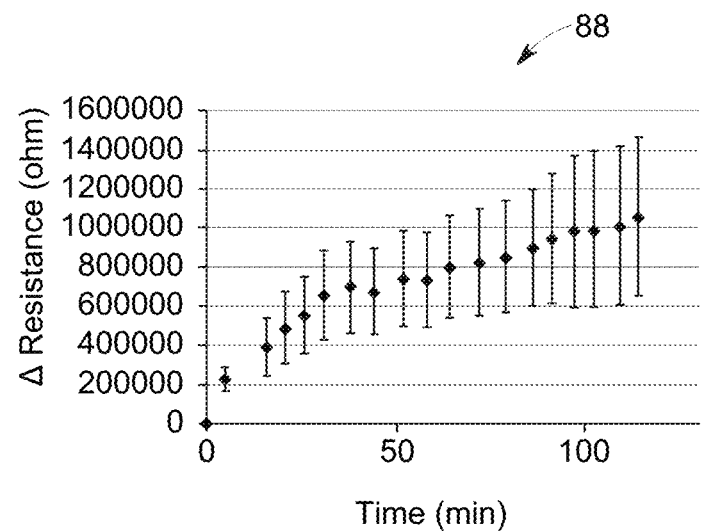
FIG. 14 is a graph showing resistance over time of the chambers of the bacteria culture array of FIG. 12, in accordance with embodiments described herein.

FIGS. 12-14 are graphs showing data collected over time regarding a sample included in the chambers of a bacteria culture array. FIG. 12 is a graph 84 shows fluorescence intensity over time, while FIG. 13 and FIG. 14 show electrical data collected at a single frequency (one kilohertz) over time. More specifically, FIG. 13 is a graph 86 that shows capacitance (in farads) over time, while FIG. 14 is a graph 88 that shows resistance over time. More specifically, the data in FIG. 13 and FIG. 14 was collected at a frequency of 1 kilohertz (kHz).

Figure 15:
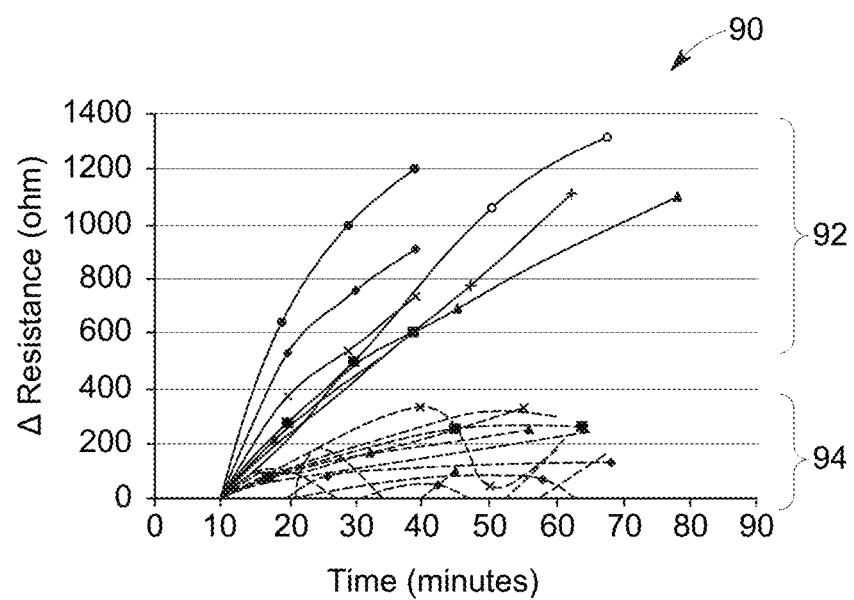
FIG. 15 is a graph showing resistance over time of chambers of a bacteria culture array that include bacteria and of chambers of the bacteria culture array that do not include bacteria, in accordance with embodiments described herein.

FIG. 15 is a graph 90 showing data collected from chambers with either one bacterium or no bacteria. More specifically, the graph 90 shows electrical resistance (in ohms) over time of two groups of chambers within a bacteria culture array. A first group of chambers that each included a single bacterium is indicated by a first portion 92 of data, and a second group of chambers that did not include any bacteria is indicated by a second portion 94 of the data.

Figure 16:
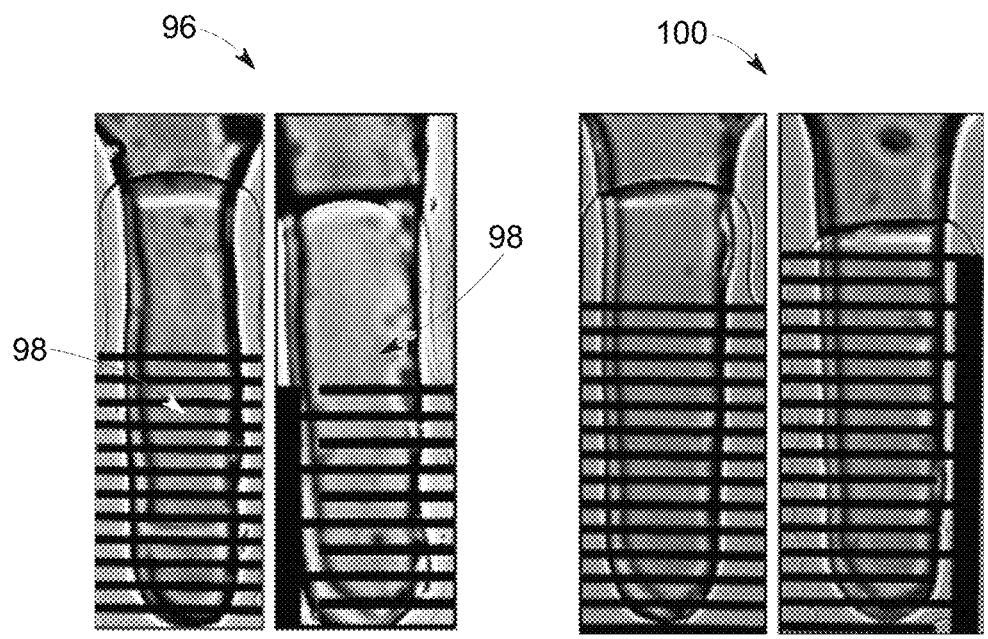
FIG. 16 is a pair of images showing the first group of chambers and the second group of chambers of FIG. 15, in accordance with embodiments described herein.

FIG. 16 is a pair of images 96, 100 showing the first group of chambers and the second group of chambers of which the data in the graph 90 is representative. The image 96 shows bacteria 98 that were located in two chambers of the first group of chambers (i.e., the group of chambers that included bacteria). The image 100 shows two chambers from the second group of chambers (i.e., the group of chambers that did not include any bacteria).

Figure 17:
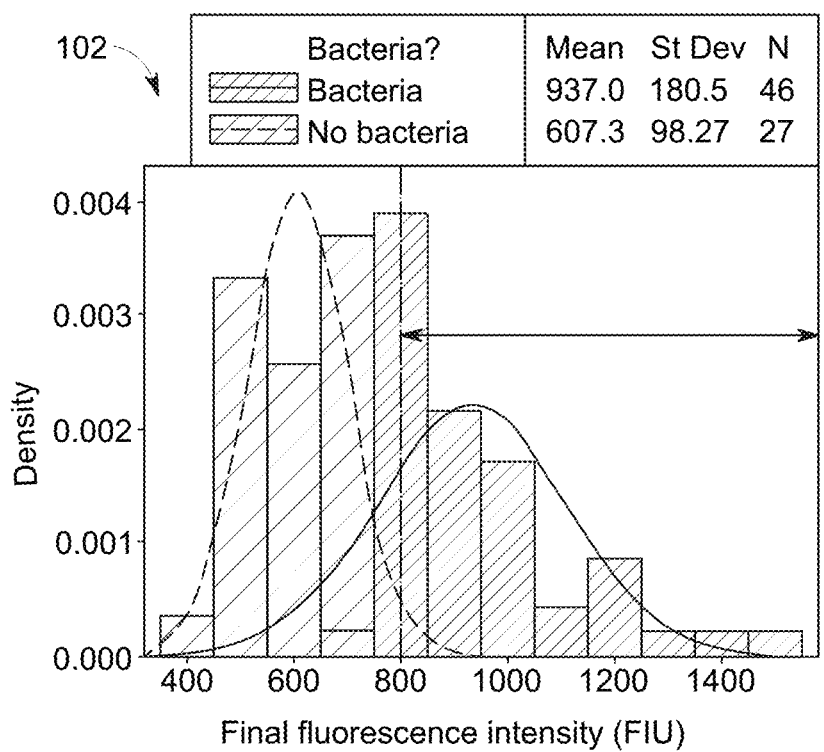
FIG. 17 is a graph showing density versus final fluorescence intensity of chambers of a bacteria culture array, in accordance with embodiments described herein.
Figure 18:
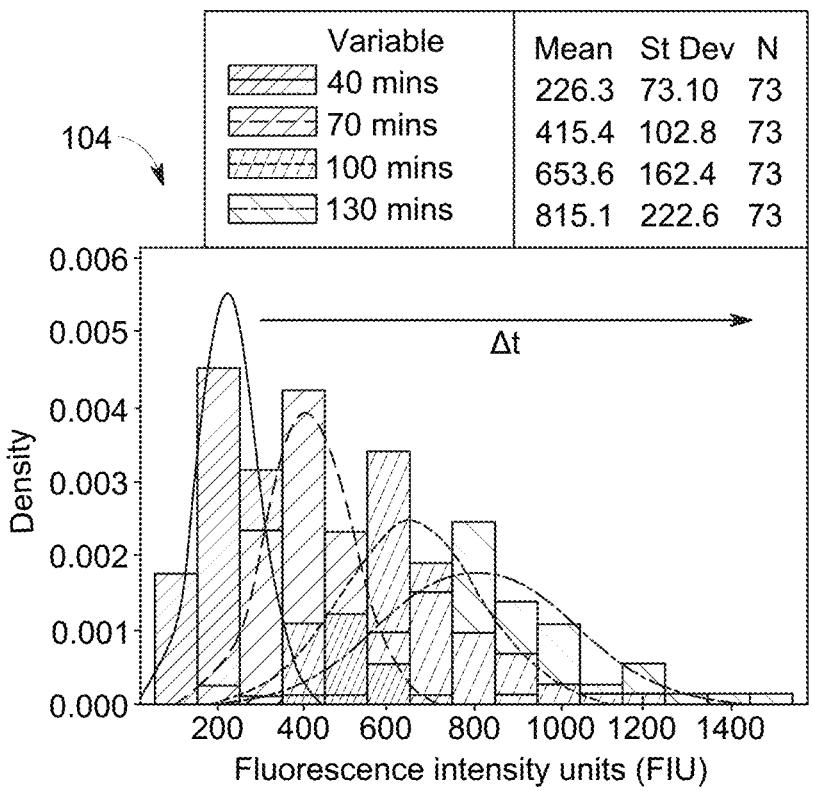
FIG. 18 is a graph showing density versus final fluorescence intensity over time of chambers of a bacteria culture array, in accordance with embodiments described herein.
Figure 19:
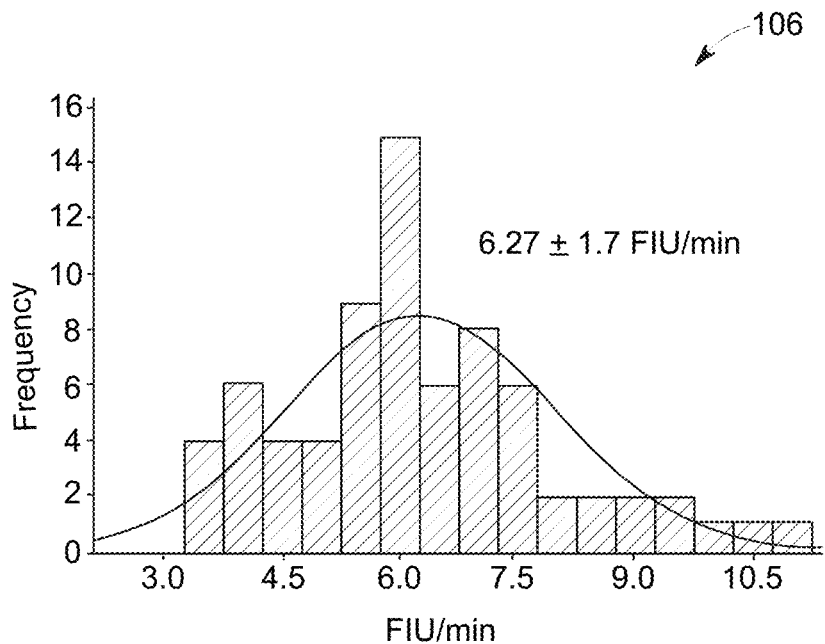
FIG. 19 is a graph showing an average metabolic signal of bacteria in chambers of a bacteria culture array, in accordance with embodiments described herein.

FIGS. 17-19 are provided from the optical control data to demonstrate that time based measurement data from experiments (e.g., the experiment of FIG. 15 and FIG. 16) may be turned into population-based and/or statistical assessments of bacteria activity (e.g., single cell bacteria activity). FIG. 17 is a graph 102 showing density versus final fluorescence intensity of chambers of a bacteria culture array. As used herein to describe FIG. 17 and FIG. 18, the term "density" refers to a proportion of chambers relative to the total number of chambers of a bacteria culture array. As shown, empty chambers (i.e., chambers without bacteria) can be distinguished from chambers with bacteria based on data collected by the sensors associated with a bacteria culture array (e.g., electrical impedance data). FIG. 18 is a graph 104 showing density versus final fluorescence intensity over time of chambers of a bacteria culture array. As shown, the average bacteria activity signal (i.e., measured fluorescence intensity) and the variance of the bacteria activity increases over time during culture of the bacteria in the bacteria culture tray. Lastly, FIG. 19 is a graph 106 showing an average metabolic signal of bacteria in chambers of a bacteria culture array. The average metabolic signal may be used to characterize bacteria at various growth conditions. While the metabolic signal used to collect the data of the graph 106 is of fluorescence intensity, measurement data of capacitance, resistance, and impedance may also be used.

Figure 20:
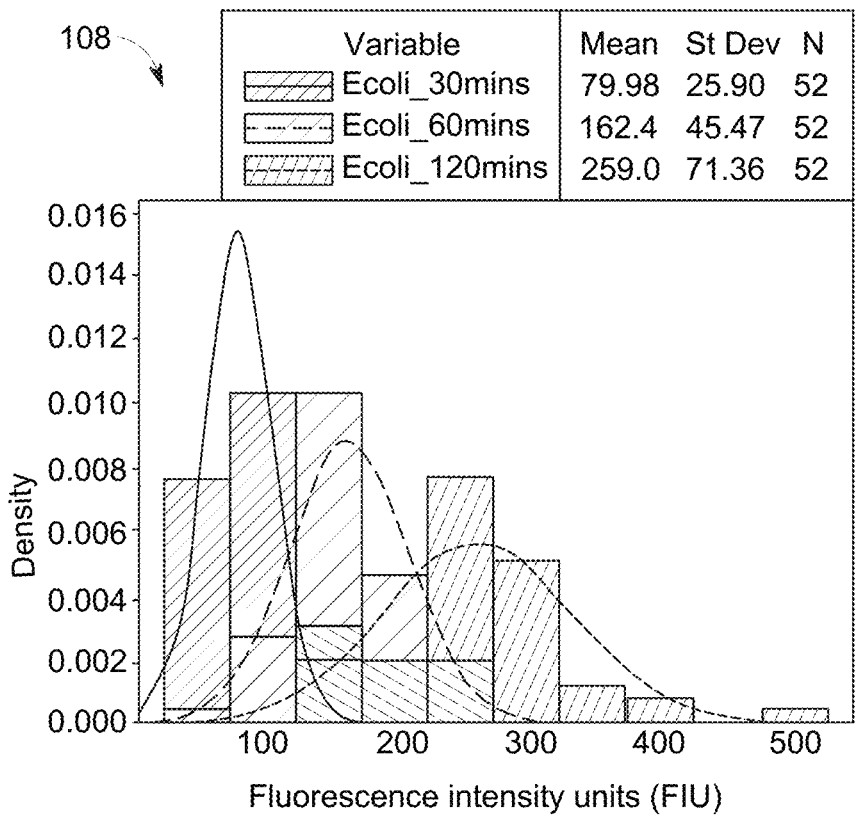
FIG. 20 is a graph showing monitoring of Escherichia coli within chambers of a bacteria culture array, in accordance with embodiments described herein.
Figure 21:
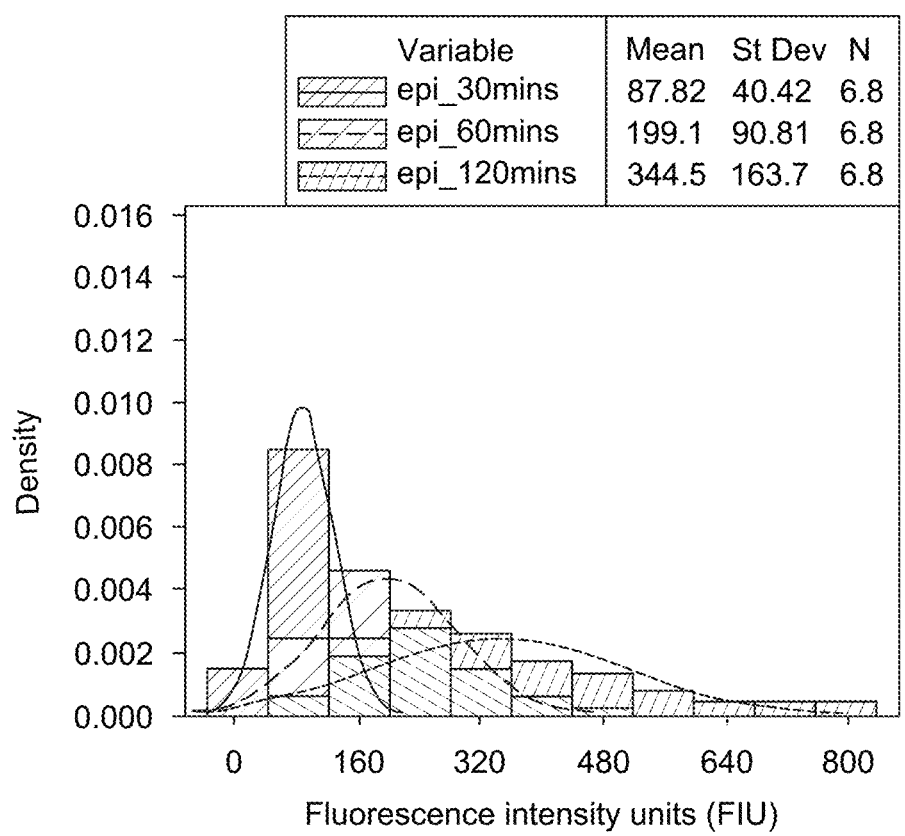
FIG. 21 is a graph showing monitoring of Staphylococcus epidermidis within chambers of a bacteria culture array, in accordance with embodiments described herein.

Additionally, the bacteria culture arrays of the present application may also be used to monitor bacteria with different doubling times. For instance, FIG. 20 is a graph 108 showing monitoring of E. coli within chambers of a bacteria culture array. E. coli has a doubling time of approximately twenty-five minutes. FIG. 21 is a graph 110 showing monitoring of Staphylococcus epidermidis (S. epidermidis) within chambers of a bacteria culture array. S. epidermidis has a doubling time of approximately fifty-one minutes. As shown in the graphs, data regarding types of bacteria with different doubling times may be collected before, during, and after the bacteria doubles.

Figure 22:
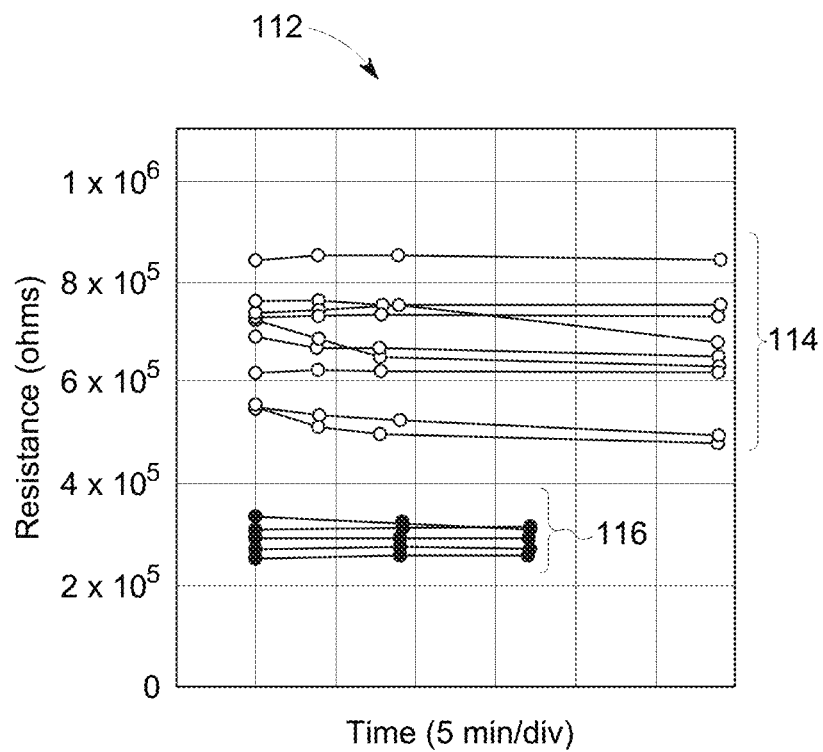
FIG. 22 is a graph showing resistance over time of chambers of a bacteria culture array that include a growth broth and chambers of the bacteria culture array that include the growth broth and bacteria, in accordance with embodiments described herein.
Figure 23:
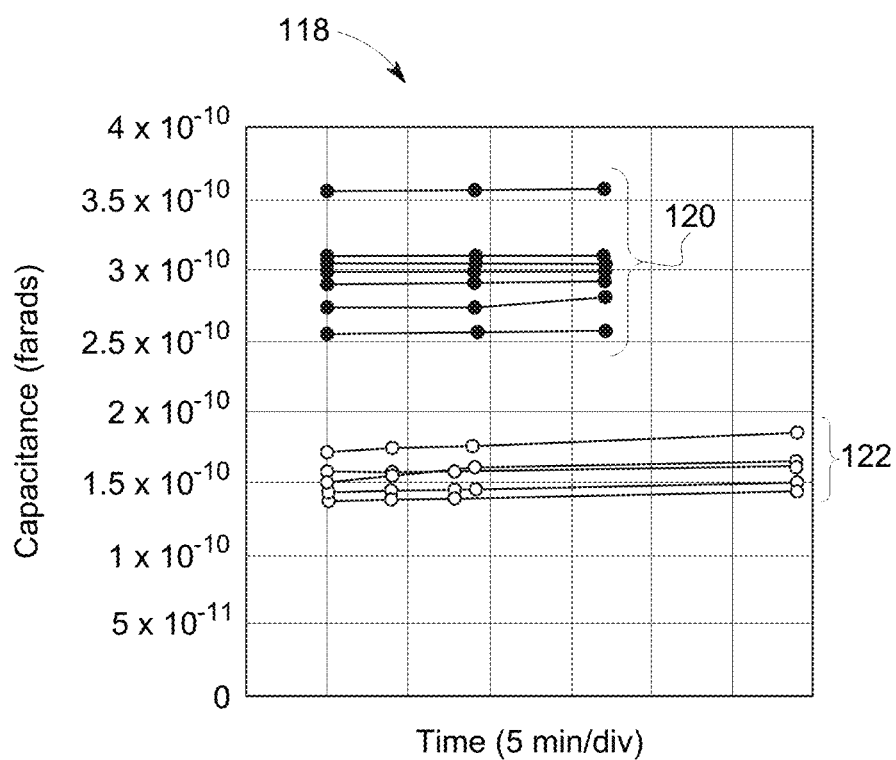
FIG. 23 is a graph showing capacitance over time of chambers of a bacteria culture array that include a growth broth and chambers of the bacteria culture array that include the growth broth and bacteria, in accordance with embodiments described herein.

Moreover, data may be collected from samples with different growth broths and media. FIG. 22 and FIG. 23 show data collected regarding chambers of a bacteria culture array. More specifically, FIG. 22 is a graph 112 showing resistance over time of chambers of a bacteria culture array loaded with a growth broth (lysogeny broth) and chambers of the bacteria culture array loaded with growth broth in which bacteria is already cultured (and then removed). The data from the chambers that only include the growth broth are shown in a first portion 114 of the data, and data from the chambers that include lysogeny broth and bacteria are shown in a second portion 116 of the data. FIG. 23 is a graph 118 showing capacitance over time of chambers of a bacteria culture array that include a growth broth and chambers of the bacteria culture array that include the growth broth after bacteria growth has already occurred. A first portion 120 of the data is representative of the chambers that include growth broth and bacteria, while a second portion 122 of the data is representative of the chambers that include growth broth only.

Figure 24:
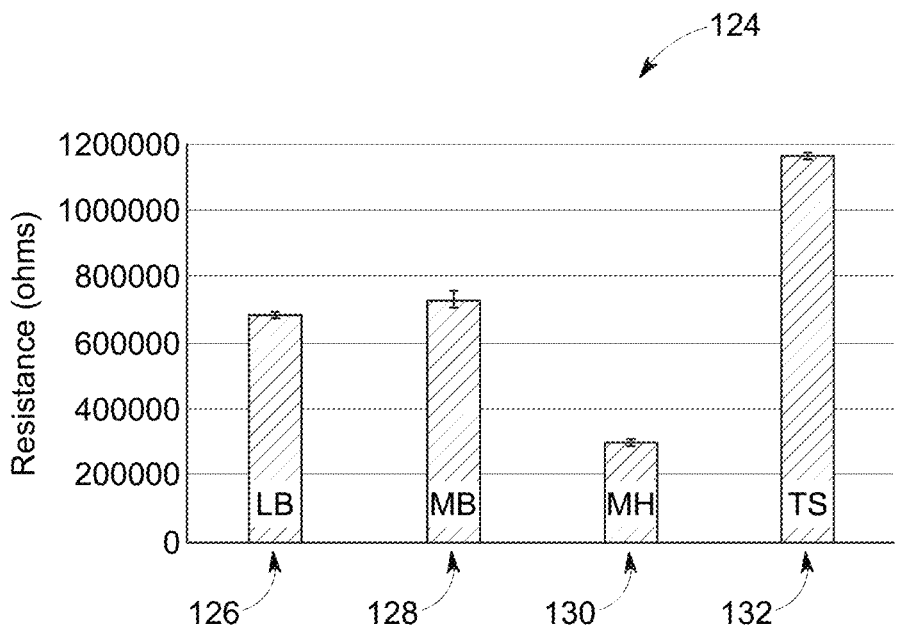
FIG. 24 is a bar graph of resistance measurements of chambers of a bacteria culture array that include different growth media, in accordance with embodiments described herein.

FIG. 24 is a bar graph 124 of resistance measurements of chambers of a bacteria culture array that include different growth media (with no bacteria present). More specifically, a first bar 126 shows data collected from chambers that included lysogeny broth, a second bar 128 shows data collected from chambers that included Middlebrook 7H9 growth broth, a third bar 130 shows data collected from chambers that included Mueller-Hinton growth medium, and a fourth bar 132 shows data collected from chambers that included tryptic soy growth broth. The sensors are capable of measuring signal from each of these common growth broths.

Figure 25:
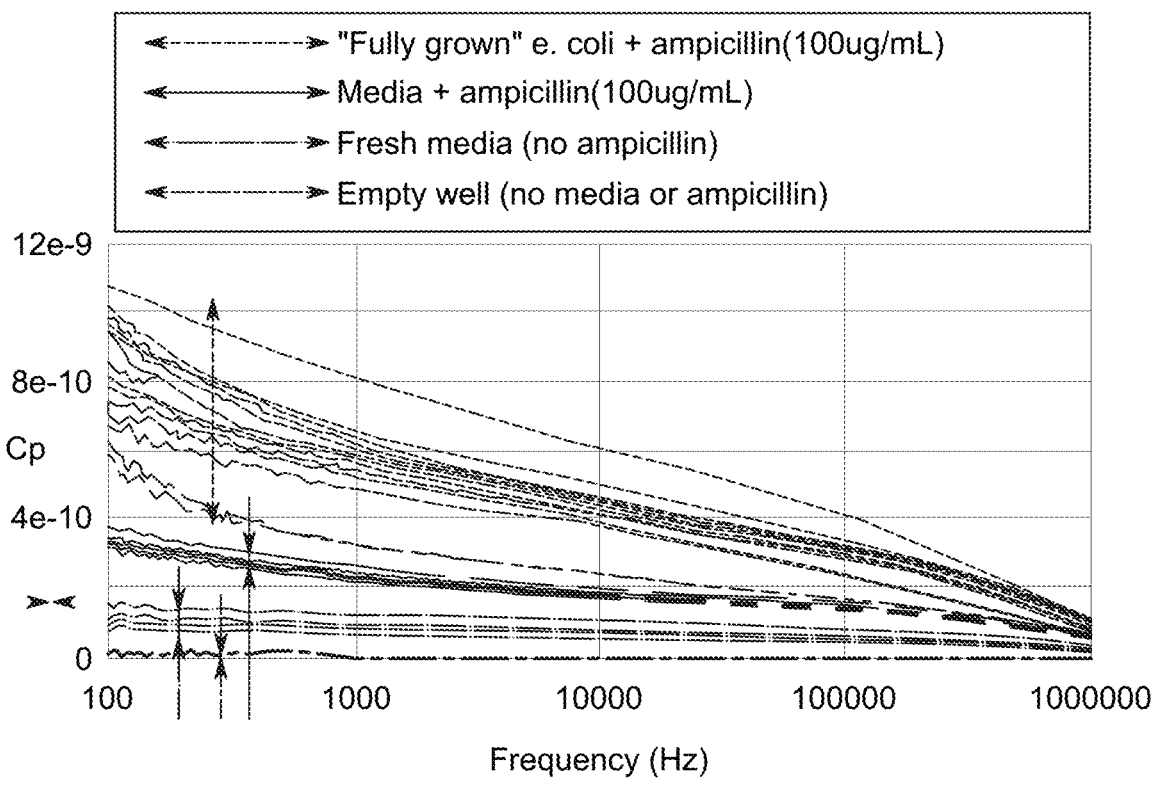
FIG. 25 is a graph showing capacitance at various frequencies of chambers of a bacteria culture array, in accordance with embodiments described herein.
Figure 26:
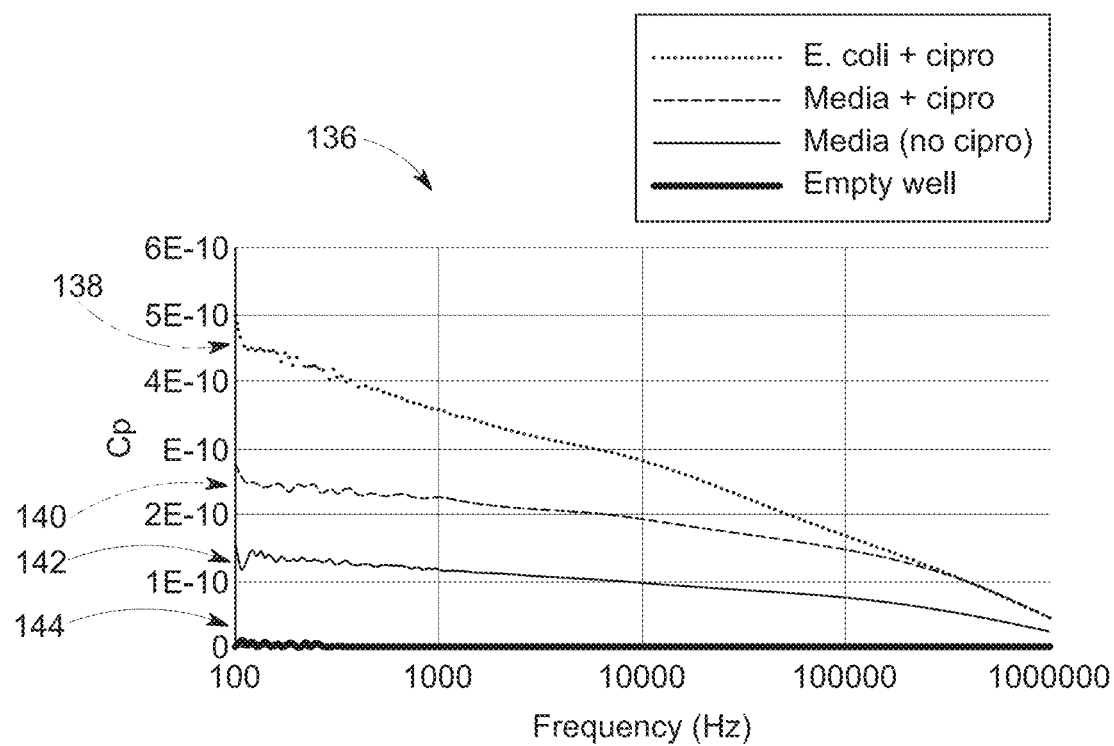
FIG. 26 is a graph showing capacitance at various frequencies of chambers of a bacteria culture array, in accordance with embodiments described herein.

Furthermore, the bacteria culture arrays of the present application may be used to measure changes in bacteria activity in the presence of growth media that includes antimicrobials. With this in mind, FIG. 25 is a graph 134 showing capacitance at various frequencies of chambers of a bacteria culture array. As shown, data from four groups of chambers is shown. One group of chambers included E. coli and growth media (tryptic soy) with ampicillin (added after E. coli growth), another group of chambers included growth media and ampicillin and no bacteria, yet another group of chambers included growth media and no ampicillin or bacteria, and a last group of chambers did not include any bacteria, growth media, or ampicillin. FIG. 26 is a graph 136 that also shows capacitance at various frequencies of chambers of a bacteria culture array. Data collected from chambers that included E. coli and growth media with ciprofloxacin (added after bacteria growth) are represented by a first portion 138 of the data. Data collected from chambers with growth media and ciprofloxacin and no bacteria are represented by a second portion 140 of the data. Also, data collected from chambers with just growth media (i.e., no bacteria or ciprofloxacin) are represented by a third portion 142 of the data, and data collected from chambers with no growth media, antimicrobials, or bacteria are represented by a fourth portion 144 of the data. These data demonstrate that the sensors are capable of differentiating chambers with and without bacteria growth even in the presence of additives, such as antimicrobials.

The disclosed techniques may provide information used by clinicians in prescribing antimicrobial treatments for patients having a bacterial infection. By assessing a sample derived from such a patient and determining to which antimicrobials the bacteria present in the sample are susceptible, the appropriate antimicrobial may be prescribed. That is, the clinician may avoid prescribing antimicrobials for the patient to which the bacteria are resistant and only select from antimicrobials to which the bacteria are susceptible. As provided herein, a sample assessed by the present techniques may be determined to be resistant to and/or susceptible to a particular antimicrobial based on a comparison of sensed data relative to a control sample without the antimicrobial or relative to baseline data acquired before contacting the sample with the antimicrobial. In addition, measurements may be taken from the bacteria culture array to first determine which chambers include viable bacteria, then an antimicrobial (or other additive that is selective for specific bacteria species and strains) may be added to determine which bacteria from the culture array show a change in growth characteristics due to the new growth environments. This data may be used to 1) quantify the number of bacteria within the bacteria culture array, 2) identify bacteria within the bacteria culture array based on growth characteristics common to that species or strain, or 3) identify minimum inhibitory concentrations (MIC) of antimicrobials (i.e., the lowest concentration of antimicrobial that statistically decreases the number of chambers selected from the sample dilution that include a growing and viable bacterium).

The disclosed techniques may also be used to assess the sterility or quality of rapid turnaround clinical products (e.g., stem cells), environmental products, food products, etc. For instance, samples may be derived from clinical, environmental, and food products, and those samples may be tested using the techniques described in the present application. Further, the disclosed techniques may be incorporated into manufacturing quality processes. Moreover, the disclosed techniques may be used for diagnostic and treatment purposes. For example, a test may be carried out using the embodiments discussed herein to determine a type of bacteria that has infected a patient. As another example, bacteria from a patient may be included in a sample to be tested using the embodiments described herein, and the effect of antimicrobial agents on the bacteria may be measured. Based on the data collected, it may be determined which antimicrobial agents may be effective in treating the patient and which antimicrobial agents would likely be ineffective for treating the patient. Such a determination may allow for a physician to prescribe medication for the patient based on the results of the test. Similarly, samples from clinical products, environmental products, food products, and manufacturing equipment and/or parts may be made, and determinations may be made based on the results of testing the samples using the technique of the present application (e.g., selecting an antimicrobial to use).

Samples to be added to the bacteria culture arrays of the present disclosure may be prepared in several ways. For example, a filter can be used to collect volumes of bacteria. The filter may subsequently be added to a centrifuge tube that includes buffer, and the centrifuge tube may be vortexed to displace bacteria from the filter. The resulting sample (i.e., solution that includes bacteria) may then be inserted into a bacteria culture array (e.g., via the inlet 52). As another example, samples may be prepared from blood via centrifugation of the blood.

Figure 27:
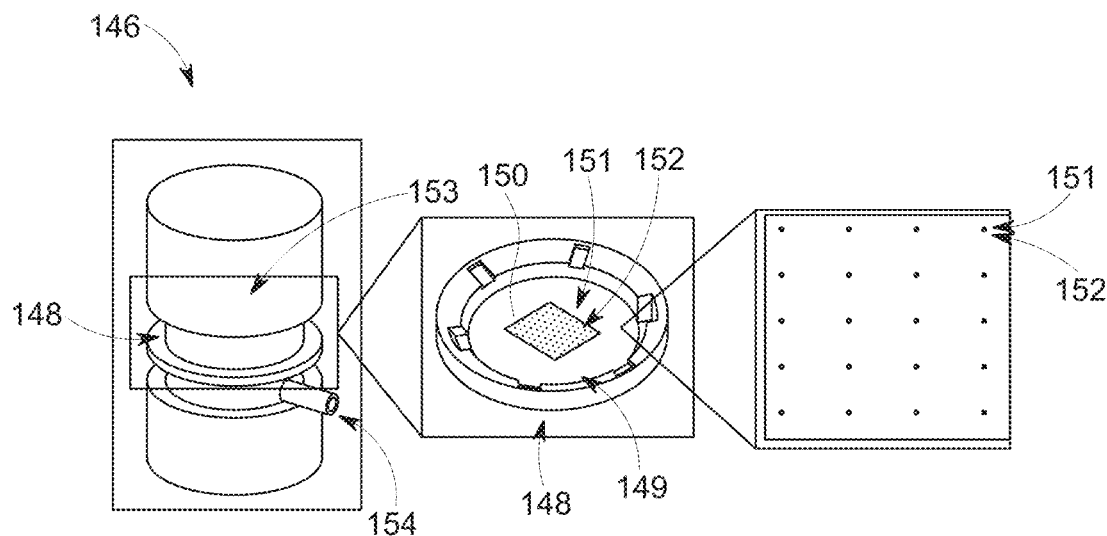
FIG. 27 is a perspective view of a system that may be used to inject samples into a bacteria culture array, in accordance with embodiments described herein.

With this in mind, FIG. 27 is a perspective view of a system 146 that may be used to inject samples into a bacteria culture array 148. A filter 149, e.g., a track etched membrane filter, may be fixed to a film layer 150. The film layer 150 may be formed from a liquid-impermeable and/or air-impermeable material, such as a polyimide film (e.g., poly (4,4-oxydiphenylene-pyromellitimide), Kapton®) that is patterned with a plurality of (e.g., 100 to 100,000) holes 151. The film layer 150 may be patterned with the holes 151 via laser machining. In another example, the bacteria culture array 148 may be formed using a silicone mold. That is, the film layer 150 may be formed by molding a silicone material over a filter layer (e.g., filter 149) such that the filter 149 and the film layer 150 form a unitary assembly. As described below in relation to FIG. 28, the holes 151 may align with pores of the filter 149 to form chambers 152 (i.e., sample sites) via openings to the chambers 152.

The film layer 150 blocks filtration of a bacteria sample 153 except in the locations of the film corresponding to the holes 151. Thus, the bacteria in the sample 153 will be pulled into the holes 151 of the film layer 150 (e.g., via a vacuum source that may be attached to an opening 154). That is, the sample may be drawn into the holes 151 of the film, meaning bacteria may enter the chambers 152 of the bacteria culture array 148. More specifically, the system 146 may allow for selective filtration of the sample 153 such that bacteria preferentially become disposed in the chambers 152 of the bacteria culture array 148. In other words, the film layer 150 and the filter 149 may selectively allow for bacteria from the sample 153 to enter the chambers 152 of the bacteria culture array 148. Furthermore, it should be noted that a sample may be loaded into chambers 152 without first removing air from the within the bacteria culture array 148 (e.g., air that occupies the chambers 152).

Figure 28:
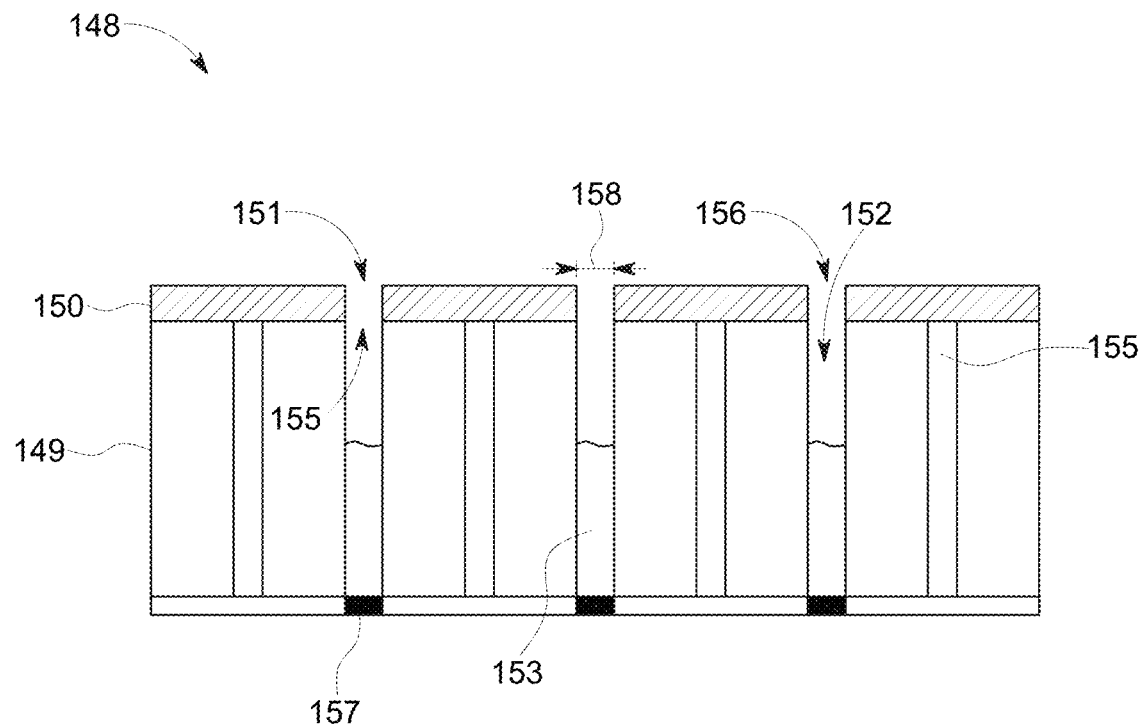
FIG. 28 is a cross-sectional diagram of a portion of the bacteria culture array of FIG. 27, in accordance with embodiments described herein.

FIG. 28 is a cross-sectional view of a portion of an embodiment of the bacteria culture array 148. As described above, the bacteria culture array 148 includes several holes 151 formed in the film layer 150, e.g., via laser machining, and the film layer 150 may be adhered or otherwise coupled to the filter 149. In the depicted arrangement, the filter 149 is arranged to be between the film layer 150 and the sensors 157. However, other arrangements are contemplated. For example, the film layer 150 may be between the filter 149 and the sensors 157 in another embodiment. In yet another embodiment, the film layer 150 is integrally molded or formed onto the filter 149. In one example, the filter 149 may be formed from a material that is water or liquid absorbent (e.g., nitrocellulose) while the film layer 150 is water or liquid-impermeable. However, it should be understood that the bacteria culture array 148 may also be implemented without the filter layer 149.

As illustrated, some of the holes 151 may cover (or, in certain embodiments may fill) pores 155 of the filter 149. However, some of the holes 151 may be aligned with the pores 155 such that the chambers 152 as well as chamber openings 156 are formed. In other words, the film layer 150 may prevent a sample 153 from entering the chambers 152 except in instances in which the holes 151 are aligned with the pores 155 of the filter 149. In such instances, the sample 153 may be drawn into the chambers 152 (e.g., via vacuum filtration), and sensors 157 may collect data regarding the sample 153. For example, the sensors 157 may collect data regarding various electrical properties such as impedance, capacitance, conductivity, and resistance, and the data may be used to make determinations regarding bacteria in the sample (e.g., resistance to an antimicrobial) in real time. Additionally, the sensors 157 may form a bottom of the chambers 152. That is, the sensors 157 may retain the sample 153 in the chambers 152. The sensors 157 may also be incorporated into the bacteria culture array 148. That is, the sensors 157 may be part of the bacteria culture array 148. However, as discussed below, the sensors 157 may be located in a housing or case in other embodiments. In certain embodiments, the sensors 157 may directly contact the sample 153 that is located in the chambers 152.

Moreover, while the illustrated embodiment shows several pores 155 that are covered by the film layer 150, it should also be noted that in other embodiments, the holes 151 may be aligned with substantially all (ninety-five percent or greater) of the pores 155. For instance, the pores 155 may have a known pattern or layout, and the holes 151 may be added to the film layer 150 based on the pattern or layout of the pores 155. As another example, more holes 151 could be added (e.g., via laser machining) to the embodiment illustrated in FIG. 28, thereby forming more chambers 152. Furthermore, the pattern of the holes 151 in the film layer 150 may be modified to control the ratio of the volume of the sample 153 that enters the chambers 152 to the surface area of the sensors 157. Additionally, the pattern of the holes 151 in the film layer 150 influences the number of bacteria that enter the chambers 152. In other words, the pattern of the holes 151 at least partially controls the number of bacteria that enter the chambers 152 as well as the ratio of the volume of the sample 153 that enters the chambers 152 to the surface area of the sensors 157.

Furthermore, it should be noted that each of the chambers 152 may include a single bacteria cell. More specifically, each of the chambers 152 may include less than two bacteria cells based on the filtration of the sample 153 as described above. However, it should also be noted that some of the chambers 152 may not include any bacteria. That is, the sample 153 in some of the chambers 152 may not include any bacteria, while in other chambers 152, the sample 153 may include bacteria (e.g., a single bacteria cell).

The holes 151 have a width 158 (i.e., a diameter) that is less than ten microns. For instance, in some embodiments, the width 158 may be one micron, two-hundred nanometers (i.e., 0.2 microns), or even smaller. However, it should also be noted that, in other embodiments, the width 158 may be equal to or larger than ten microns (e.g., twenty microns, fifty microns, one hundred microns or larger).

It should also be noted that the width 158 of the holes 151 and the pores 155 may be different. For instance, the pores 155 may be smaller than the holes 151 in some embodiments, while in other embodiments, the holes 151 may be smaller than the pores 155. In one embodiment, the filter 149 is configured to absorb or hold the sample until selective entry into the chambers 152 via the film layer 150. Additionally, in one embodiment, the chambers 152 have a volume that ranges from 1 picoliter to fifty thousand picoliters (i.e., 50 nanoliters), while in another embodiment, the chambers 152 have a volume ranging from 100 picoliters to 50,000 picoliters. In other words, the chambers 152 are sized to accommodate a fluid volume equal to or less than fifty nanoliters. However, it should be noted that in some embodiments, the volume of the chambers 152 may be larger than five nanoliters. Further, the film layer 150 may be configured such that the material of the film layer 150, aside from the holes 151, is impermeable to the sample 153, e.g., impermeable to passage of bacteria or liquid through the film layer 150, except for locations where the holes 151 are formed.

Figure 29:
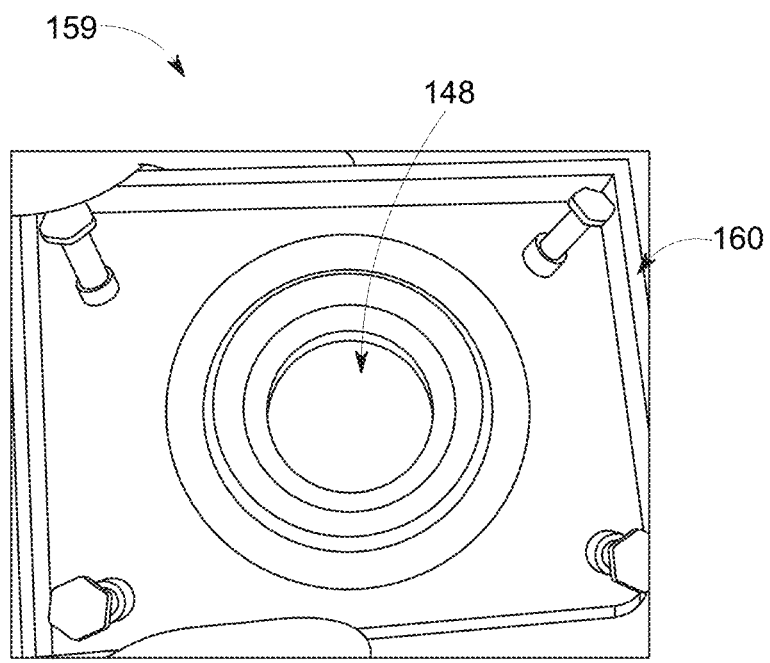
FIG. 29 is an illustration of a device that includes the bacteria culture array of FIG. 27, in accordance with embodiments described herein.

The bacteria culture array 148, as discussed above, may be included in a device. More specifically, FIG. 29 is an illustration of a device 159 that includes the bacteria culture array 148. In other words, the bacteria culture array 148 may be removed from the system 146 and placed inside of a case 160 (e.g., a housing), which may be made from plastic or glass. The case 160 may completely encase the bacteria culture array. Additionally, the case 160 may also include the sensors 157 that are used to collect data from the chambers of the bacteria culture array 148. However, it should also be noted that, in other embodiments, the case 160 may include components that couple to the sensors of the bacteria culture array 148 to allow for data collected by the sensors 157 to be transmitted to a monitoring and analytical system. In other words, the sensors 157 may be included in the bacteria culture array 148, and the case 160 may be coupled to the sensors and a system that is used to monitor and/or analyze data collected by the sensors. In any case, it should be noted that the bacteria culture array 148 and the case 160 are portable. Additionally, the bacteria culture array 148 and/or the case 160 may be disposable. That is, after a bacteria culture array 148 and/or case 160 has been used, the bacteria culture array 148 and/or the case 160 may be discarded by the user.

Figure 30:
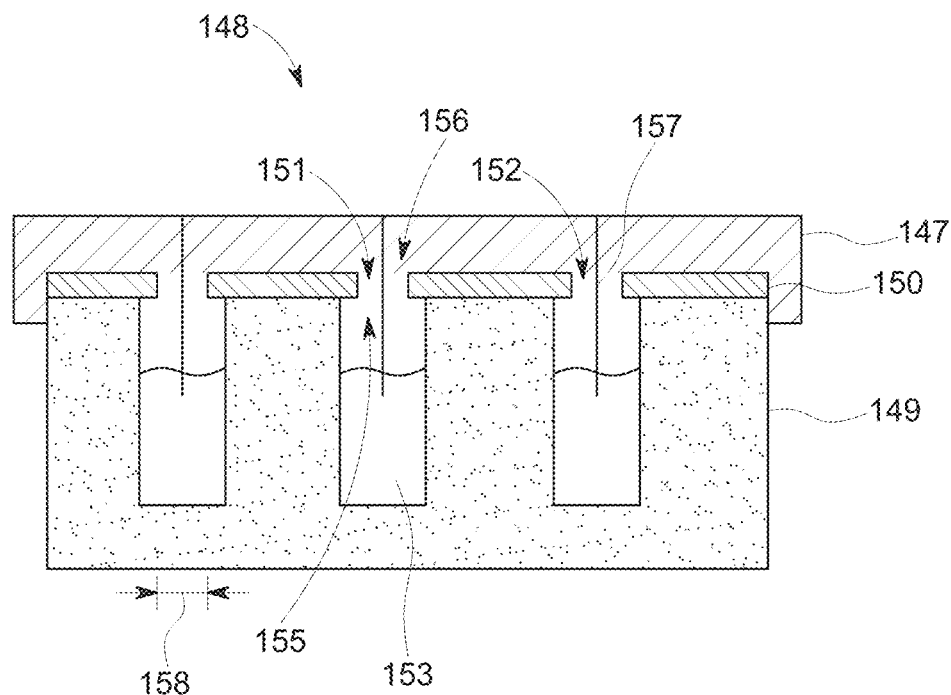
FIG. 30 is a cross-sectional diagram of a portion of a bacteria culture array of FIG. 27, in accordance with embodiments described herein.

In other embodiments, the case 160, including the sensors 157, may be retained to be cleaned and reused with another sample. For example, FIG. 30 is cross-sectional diagram of another embodiment of the bacteria culture array 148. The bacteria culture array 148 may be encased within the case 160 that includes and a lid 147. The lid 147 includes the sensors 157 and may be placed such that the sensors 157 fit into the chambers 156 and contact the sample 153. As also illustrated, the holes 151 in the film layer 150 may be narrower (i.e., have a smaller diameter) than the pores 156 of the filter 149.

Figure 31:
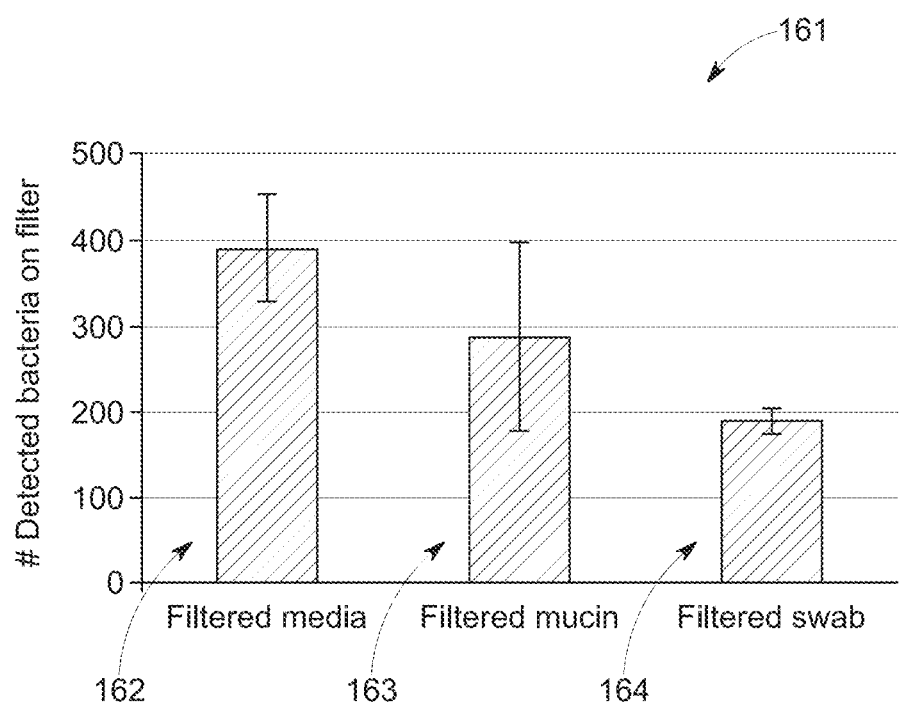
FIG. 31 is a graph showing numbers of bacteria detected on bacteria culture arrays for several means of adding bacteria to the bacteria culture arrays, in accordance with embodiments described herein.

Continuing with the drawings, FIG. 31 is a graph 161 showing numbers of bacteria detected on bacteria culture arrays (e.g., bacteria culture array 148) using the system 146 based on the manner of preparing a sample (e.g., sample 153). A first bar 162 in indicative of data from a sample prepared from a tryptic soy growth media bacteria culture. A second bar 163 is indicative of data from bacteria cultured in tryptic soy growth media with added mucin. A third bar 164 is indicative of data from a mock nasal swab. More specifically, the mock nasal swab included mucin at physiological viscosity and concentration and *E. coli*. A swab was used to collect a sample, and the sample was incubated in a buffer, agitated, and filtered into the chambers of a bacteria culture array.

Figure 32:
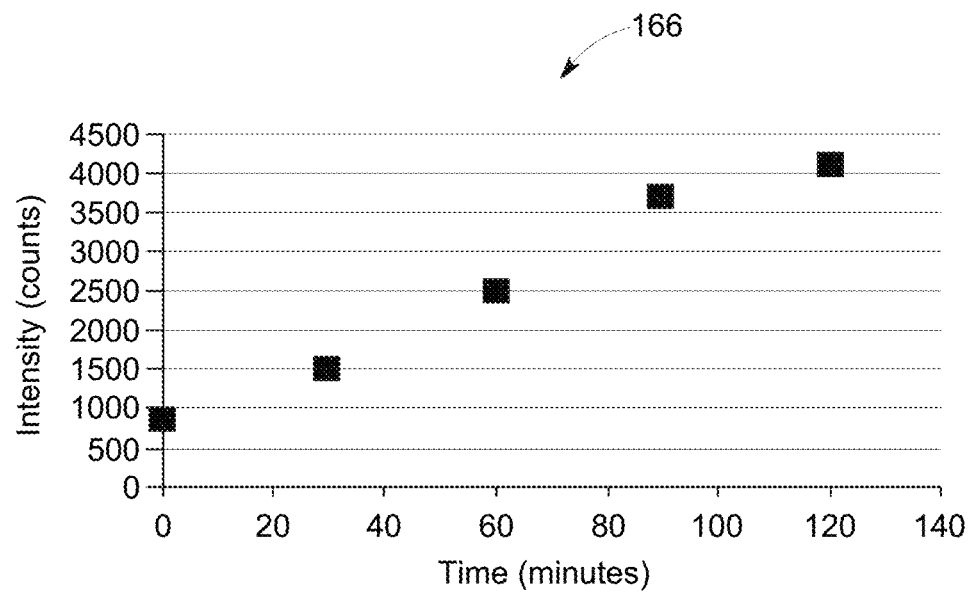
FIG. 32 is a graph showing growth of bacteria samples within chambers of a bacteria culture array, in accordance with embodiments described herein.

Bacteria may be cultured in the chambers of bacteria culture arrays (e.g., bacteria culture array 148). Indeed, FIG. 32 is a graph 166 showing growth of bacteria samples within chambers of a bacteria culture array. More specifically, the graph 166 shows fluorescence over time of a bacteria sample that included a fluorescence indicator.

Figure 33:
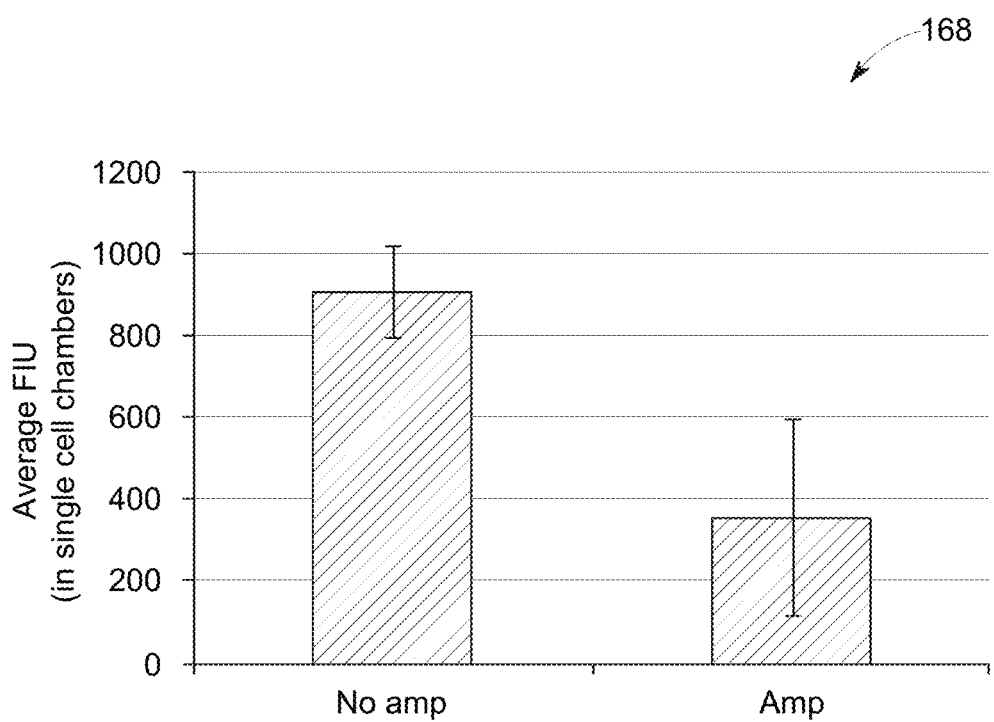
FIG. 33 is a graph showing bacteria growth within chambers of a bacteria culture array that do not include an antimicrobial as well as growth within chambers of the bacteria culture array that include ampicillin, in accordance with embodiments described herein.

Furthermore, the bacteria culture arrays of the present disclosure may be used to assess the effect of drugs on bacteria samples. For instance, single cells of bacteria may be added the chambers of a bacteria culture array, and drugs and/or antimicrobial agents may be added to some or all of the chambers. In other words, single cell bacteria activity may be used to conduct population-based analysis of bacteria samples. With this in mind, FIG. 33 is a graph 168 showing bacteria growth within chambers of a bacteria culture array. Some of the chambers included ampicillin, while other chambers did not include any ampicillin. As the graph 168 indicates, data regarding the chambers was collected, and the hindrance to growth caused by the ampicillin was detected.

As such, the bacteria culture array may be used for a variety of applications. For instance, the bacteria culture array may be used to select healthy and/or viable bacteria for analysis. Additionally, the bacteria culture array may be used to distinguish between species and/or strains of bacteria. Moreover, the bacteria culture array may also be used to make determinations regarding growth conditions (e.g., selection of growth media). Furthermore, when varying concentrations of drugs are used, the bacteria culture array may be used to determine drug concentrations at which bacteria are and/or are not affected by the drugs. Also, it should be noted that, as shown in the graph 168, bacteria added to the bacteria culture array can be cultured in a short amount of time (e.g., minutes to hours) before being tested/analyzed.

Figure 34:
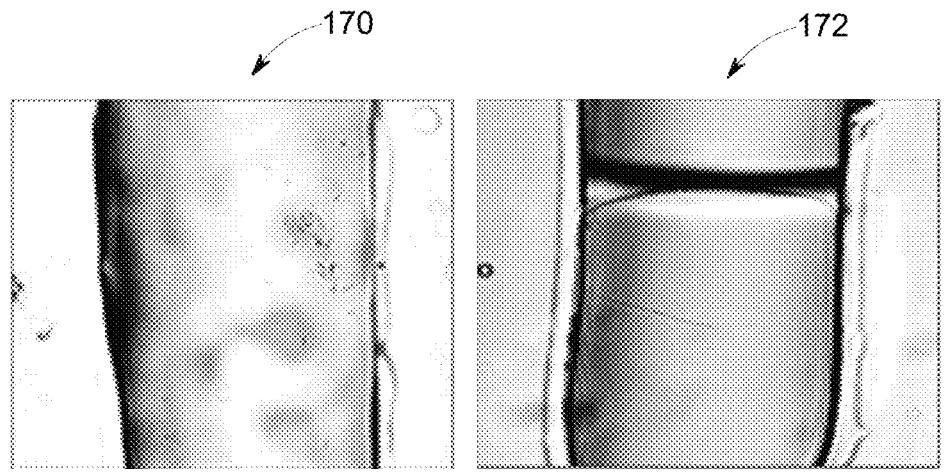
FIG. 34 is images of chambers in the bacteria culture array of FIG. 32, in accordance with embodiments described herein.

Visual confirmation of the results shown in the graph 168 were also obtained. FIG. 34 is images 168, 170 of the chambers of the bacteria culture array. The image 170 shows a chamber that did not include ampicillin, while the image 172 shows a chamber that did include ampicillin.

Figure 35:
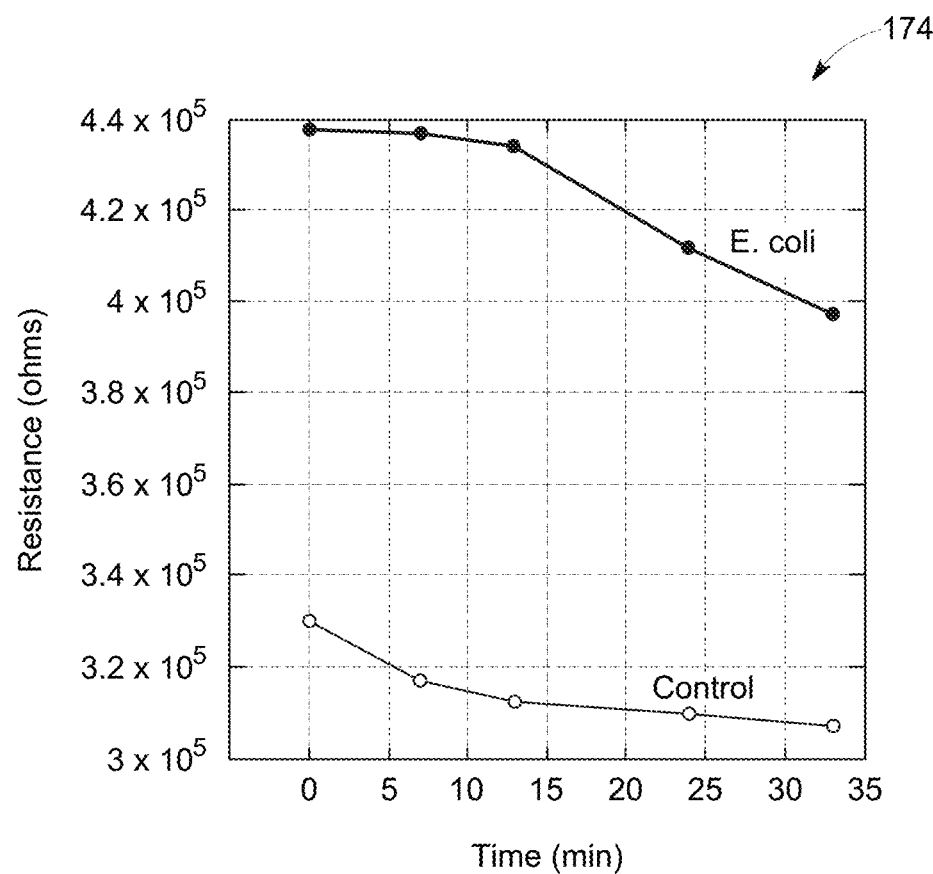
FIG. 35 is a graph of resistance over time of chambers in a bacteria culture array, in accordance with embodiments described herein.

As another example of the capabilities of the bacteria culture array, metabolic activity of bacteria from a complex sample may be obtained. For instance, a sample of *E. coli* in growth media was collected with a nasal swab and filtered into a bacteria culture array (e.g., using the system 146). Indeed, FIG. 35 is a graph 174 of resistance data collected using techniques disclosed above. The graph 174 also includes data from a (i.e., "control"). After a ten minute loading period, the data indicates a decrease in resistance of the sample that included *E. coli*, which would occur due to cell activity/metabolism.

Figures 38, 39:
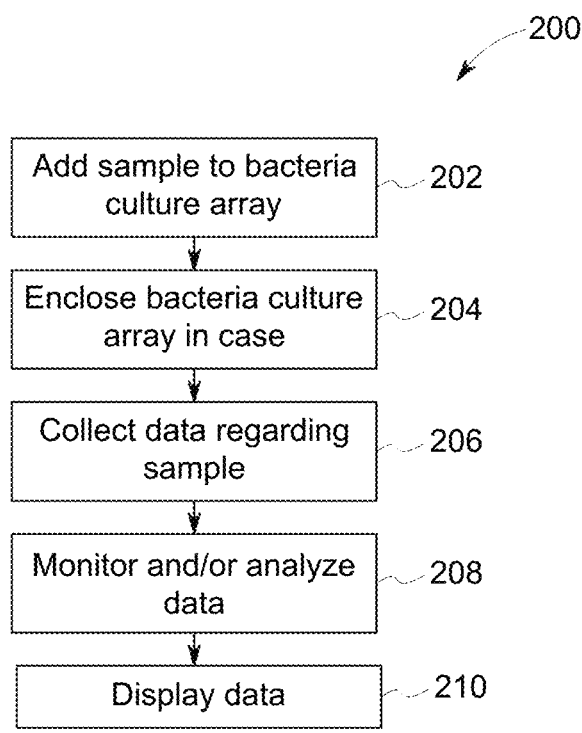
FIG. 38 is a spreadsheet 184 of resistance measurements taken from a bacteria culture array with chambers that included bacteria and an antimicrobial agent, in accordance with embodiments described herein.
FIG. 39 is a flow chart of a method for filling a bacteria culture array with a sample and monitoring and/or analyzing the sample, in accordance with embodiments described herein.

As another example of data that may be collected, FIGS. 36-38 are spreadsheets of resistance data collected from chambers of a bacteria culture array. Each data cell in the spreadsheets of FIGS. 36-38 reflects a measured resistance value of a chamber of the bacteria culture array. Referring specifically to FIG. 36, which is a spreadsheet 176 with a column 178 of data cells reflecting resistance measurements of chambers of a bacteria culture array that included tryptic soy broth. The spreadsheet 176 also includes a group 180 of data cells that reflect resistance data from chambers of a bacteria culture array, some of which included *E. coli* and tryptic soy broth. Statistical analysis of the data reflect in the spreadsheet 176 may be used to determine which chambers included bacteria. For instance, a baseline (e.g., background) of the growth medium may be determined (e.g., an average value of the chambers plus or minus a standard deviation), and data cells that differ from the baseline by at least three standard deviations are indicative chambers that include bacteria. For example, data cell 182 and the other unshaded data cells correspond to chambers in the bacteria culture array that included bacteria, while data cell 184 and the other shaded data cells correspond to chambers in the bacteria culture array that do not include bacteria.

As discussed above, data from the bacteria culture array may also be used to determine whether a bacteria sample is resistant to an antimicrobial agent. FIG. 37 is a spreadsheet 186 of resistance measurements taken from a bacteria culture array with chambers that included bacteria (e.g., *E. coli*) and an antimicrobial agent (e.g., ampicillin). Additionally, FIG. 38 is a spreadsheet 192 reflecting resistance measurements from chambers of a bacteria culture array that included *E. coli* and a different microbial agent, kanamycin. Data from the bacteria culture array may be analyzed in a manner that is the same as or similar to the manner described above with relation to FIG. 36. That is, a baseline may be established (e.g., by taking measurements at a first time), and later data measurement (e.g., a measurement taken at a second time) may be compared to the baseline. That is, data collected at the second time may be compared to the data collected at the first time in order to make such determinations. Data cells 188, 194 and the other unshaded data cells correspond to chambers that included bacteria that grew in the presence of an antimicrobial. Data cells 190, 196 and the other shaded data cells correspond to chambers that included bacteria that did not grow in the presence of an antimicrobial agent. In other words, a statistical decrease in the number of growing and viable bacteria cells at any given growth period of time would represent susceptibility of the bacteria population to the antimicrobial.

Continuing to the next drawing, FIG. 39 is a flow chart of a method 200 for filling a bacteria culture array with a sample and monitoring and/or analyzing the sample. The steps of the method 200 may be performed in any suitable order. Additionally, the method 200 may be carried out using the various embodiments of bacteria culture arrays discussed above. With this in mind, at block 202, a sample may be added to chambers of a bacteria culture array. For example, as discussed above, the bacteria culture array may include one or more filling channels that include the chambers, and a sample may be added to the chambers via the filling channels. As another example, and as also described above, the sample may be filtered through a film that includes holes through which the sample may pass.

At block 204, the bacteria culture array may be enclosed within a case. As mentioned above, the case may be made from materials such as plastic and glass. In some embodiments, enclosing the bacteria culture array within the case may include using a lid to cover the bacteria culture array.

At block 206, the data regarding the sample in the chambers of the bacteria culture array may be collected. For instance, sensors, which, as described above, may be part of the bacteria culture array or the case, may be used to collect the data. Additionally, and as also described above, the sensors may be at least partially disposed within the chambers and come into physical contact with the sample. In some embodiments, each sensor may collect data regarding a single bacteria cell (e.g., from a chamber that does not include more than one bacteria cell). In any case, the data may be collected over a period of time, and multiple measurements may be taken. For example, data may be collected constantly or at intervals (e.g., every five minutes).

At block 208, the data from the sensors may be monitored and/or analyzed by a processor. In other words, data from each chamber associated with a sensor may be collected. For example, the processor may be configured to execute software instructions that cause the processor to monitor and/or analyze the data. As a more specific example, the data from the sensors may include data representative of a measurement (e.g., impedance), and the processors may analyze the data. For instance, the data collected at a first time may be compared to data collected at another time (e.g., a later time) as part of the analysis. That is, data may be compared to a baseline that based on the data collected at the first time.

At block 210, the data collected by the sensors may be displayed, for example, on a monitor or a graphical user interface. Moreover, the results of the analysis may also be displayed with the data that is collected by the sensors. It should further be noted that the method 200 may also include identifying chambers based on the comparison of the data collected at a later time to the baseline. For example, the chambers may be identified based the comparison of data between two point in time corresponding to bacterial growth, bacterial death, antimicrobial resistance, and the like.

Technical effects of the subject matter disclosed herein include, but are not limited to, systems and methods for single cell, population-based sensing of bacteria metabolism. In particular, samples that include bacteria may be loaded into chambers of a bacteria culture array, and data regarding the sample may be collected. Additionally, bacteria may be cultured within the bacteria culture arrays in minutes or hours. Thus, the bacteria culture arrays described herein may be used to select healthy and/or viable bacteria for analysis, distinguish between species and/or strains of bacteria, make determinations regarding growth conditions (e.g., selection of growth media), and, when concentrations of drugs are included in the chambers, the bacteria culture array may be used to determine drug concentrations at which bacteria are and/or are not susceptible to the drugs.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A system, comprising: a bacteria culture array comprising a plurality of chambers each configured to receive a portion of a sample comprising bacteria, wherein each individual chamber of the plurality of chambers comprises a chamber opening configured to permit access of the portion of the sample to the individual chamber, and wherein each individual chamber is separated from the other individual chambers by a filling channel;
   one or more sensors configured to collect data from the individual chamber, wherein the one or more sensors are configured to contact the sample;
   a monitoring and analysis system comprising a processor configured to: receive the data from the one or more sensors at a first time and a second time; compare the data received at the second time to the data received at the first time; and identify a portion of the plurality of chambers of the bacteria culture array based on the comparing.

2. The system of claim 1, wherein each chamber of the plurality of chambers is sized to accommodate a fluid volume of five nanoliters or less.

3. The system of claim 1, comprising a case configured to encompass the plurality of chambers of the bacteria culture array.

4. The system of claim 3, wherein the one or more sensors of the plurality of chambers are disposed on the case.

5. The system of claim 1, wherein each of the one or more sensors is configured to physically contact the portion of the sample of the plurality of chambers.

6. The system of claim 1, wherein the bacteria culture array comprises a film layer comprising a plurality of holes, wherein respective individual holes of the plurality of holes are aligned with respective chamber openings.

7. The system of claim 6, wherein each hole of the plurality of holes is 1 micron in diameter or less.

8. The system of claim 6, wherein the film layer is impermeable to the bacteria in areas surrounding the plurality of holes, and the pattern of the holes on the film layer influences the number of bacteria that enter each chamber of the plurality of chambers.

9. The system of claim 1, wherein the monitoring and analysis system comprises an impedance analyzer or an LCR meter.

10. The system of claim 1, wherein the plurality of chambers are configured to receive the sample without first removing air from the plurality of chambers.

11. A method, comprising: providing a bacteria culture array comprising a plurality of individually addressable sensors, wherein each individual sensor of the plurality of individually addressable sensors is configured to be in contact with a respective sample site of the bacteria culture array, and wherein the sample sites are not in direct contact with each other;
contacting, at an initial time, the bacteria culture array with a sample comprising bacteria such that the sample is distributed throughout the bacteria culture array onto the respective sample sites and such that each respective sample site receives one bacterial cell or less from the sample;
receiving data from the plurality of individually addressable sensors over time;
comparing the data from the plurality of individually addressable sensors to a baseline representative of the initial time; and
identifying individual sample sites in the bacteria culture array based on the comparing.

12. The method of claim 11, wherein one or more of the respective sample sites do not comprise any bacterial cells.

13. The method of claim 11, wherein contacting the bacteria culture array with the sample comprises passing the sample through holes of a film layer of the bacteria culture array.

14. The method of claim 11, wherein the bacteria culture array comprises a filter layer disposed within or adjacent to the film layer.

15. The method of claim 11, comprising contacting the samples sites with an antimicrobial agent.

16. The method of claim 15, comprising comparing data associated with the at least one respective sample sites to another of the respective sample sites.

17. The method of claim 15, comprising comparing baseline data before the contacting to data after the contacting from the plurality of individually addressable sensors.

18. The method of claim 11, comprising fitting the data from at least one sensor to a data curve associated with bacterial growth, bacterial death, a growth medium, or an antimicrobial agent and providing an assessment of the sample based on the fitting.

19. A method, comprising: loading a sample comprising bacteria into a plurality of chambers of a bacterial culture array via a filling channel such that a first portion of the plurality of chambers comprises the sample, wherein each chamber of the plurality of chambers comprises a sensor of a plurality of sensors configured to collect data regarding a property of each respective chamber; loading a fluid into the filling channel such that a meniscus is formed in each chamber of the first portion of the plurality of chambers; and collecting data via the plurality of sensors.

20. The method of claim 19, comprising loading the sample into the filling channel such that a second portion of the plurality of chambers comprises the sample, wherein the meniscus prevents the sample from entering the chambers of the first portion.

* * * * *